(12) United States Patent
Linder et al.

(10) Patent No.: US 11,597,750 B2
(45) Date of Patent: Mar. 7, 2023

(54) METHOD FOR PRODUCING A CONDENSED ADHESIVE PHASE OF SILK FUSION PROTEINS

(71) Applicant: Aalto University Foundation sr, Aalto (FI)

(72) Inventors: Markus Linder, Aalto (FI); Pezhman Mohammadi, Aalto (FI); Sesilja Aranko, Aalto (FI)

(73) Assignee: Aalto University Foundation sr, Aalto (FI)

( * ) Notice: Subject to any disclaimer, the term of this patent is extended or adjusted under 35 U.S.C. 154(b) by 104 days.

(21) Appl. No.: 16/622,301

(22) PCT Filed: Jun. 13, 2018

(86) PCT No.: PCT/FI2018/050460
§ 371 (c)(1),
(2) Date: Dec. 13, 2019

(87) PCT Pub. No.: WO2018/229341
PCT Pub. Date: Dec. 20, 2018

(65) Prior Publication Data
US 2020/0325188 A1    Oct. 15, 2020

(30) Foreign Application Priority Data

Jun. 13, 2017 (FI) ........................... 20175544
Dec. 22, 2017 (FI) ........................... 20176165

(51) Int. Cl.
| | | |
|---|---|---|
| *C07K 14/435* | (2006.01) | |
| *C07K 1/02* | (2006.01) | |
| *C07K 14/33* | (2006.01) | |
| *D01D 1/02* | (2006.01) | |
| *D01F 4/00* | (2006.01) | |
| *C12N 15/62* | (2006.01) | |
| *A61L 27/36* | (2006.01) | |

(52) U.S. Cl.
CPC .......... *C07K 14/43518* (2013.01); *C07K 1/02* (2013.01); *C07K 14/33* (2013.01); *D01D 1/02* (2013.01); *D01F 4/00* (2013.01); *C07K 2319/00* (2013.01); *D10B 2211/04* (2013.01)

(58) Field of Classification Search
CPC ................................................. C07K 2319/00
See application file for complete search history.

(56) References Cited

U.S. PATENT DOCUMENTS

| 7,951,908 B2 | 5/2011 | Scheibel et al. | |
|---|---|---|---|
| 8,173,772 B2 | 5/2012 | Johansson et al. | |
| 2007/0196429 A1* | 8/2007 | Scheibel | A61L 27/227 424/426 |
| 2014/0031526 A1* | 1/2014 | Shoseyov | D01F 9/00 530/356 |
| 2015/0087046 A1* | 3/2015 | Hedhammar | C07K 14/36 435/325 |
| 2017/0312387 A1* | 11/2017 | Alessandrino | A61L 27/227 |
| 2018/0298523 A1* | 10/2018 | Perez Rigueiro | D01D 4/02 |

FOREIGN PATENT DOCUMENTS

WO    WO2011115538 A1    9/2011

OTHER PUBLICATIONS

Dinjaski et al. (2017) Osteoinductive recombinant silk fusion proteins for bone regeneration, Acta Biomater., vol. 49, pp. 127-139.*
Tormo et al. (1996) Crystal structure of a bacterial family-III cellulose-binding domain: a general mechanism for attachment to cellulose, EMBO J., vol. 15, No. 2, pp. 5739-5751.*
Scheible T. (2004) Spider silks: recombinant synthesis, assembly, spinning, and engineering of synthetic proteins, Microbial Cell Factories, vol. 3, issue 14, pp. 1-10.*
Adrianos et al: Nephila clavipes flagelliform silk-like GGX motifs contribute to extensibility and spacer motifs contribute to strength in synthetic spider silk fibers. Biomacromolecules, 2013, vol. 14, pp. 1751-1760.
Albertson et al: Effects of different post-spin stretching conditions on the mechanical properties of synthetic spider silk fibers. J. Mech. Behav. Biomed. Mater, 2014, vol. 29, pp. 225-234.
Ebrahimi et al: Silk-Its Mysteries, How It Is Made, and How It Is Used. ACS Biomater. Sci. Eng, 2015, vol. 1, pp. 864-876.
Exler et al: The amphiphilic properties of spider silks are important for spinning. Angewandte Chemie (Intern. Ed.in English), 2007, vol. 46, No. 19, pp. 3559-3562.
Gnesa et al: Conserved C-terminal domain of spider tubuliform spidroin 1 contributes to extensibility in synthetic fibers. Biomacromolecules, 2012, vol. 13, pp. 304-312.
Green et al: Molecular cloning—A laboratory manuel. 2012, vol. 1.
Hedhammar et al: Structural Properties of Recombinant Nonrepetitive and Repetitive Parts of Major Ampullate Spidroin 1 from Euprosthenops australis: Implications for Fiber Formation †. Biochemistry, 2008, vol. 47, pp. 3407-3417.

(Continued)

*Primary Examiner* — Suzanne M Noakes
*Assistant Examiner* — Jae W Lee
(74) *Attorney, Agent, or Firm* — Laine IP Oy

(57) ABSTRACT

The present invention is directed to a method for producing a condensed phase of a silk fusion protein, the method comprising the steps of preparing a solution of a silk fusion protein in an aqueous medium and concentrating the silk fusion protein in the aqueous medium, wherein the fusion protein is isolated from a recombinant production host and comprises a silk-like protein sequence and two separate non-silk terminal module sequences, such as cellulose binding modules, SpyCatcher domains, tenth type III module of Fibronectin, gamma-crystallin D, flanking the silk-like protein sequence; wherein the method is performed so that the silk fusion protein is not precipitated and subsequently dissolved to the aqueous medium. The present invention is also directed to using such fusion proteins as adhesives.

15 Claims, 10 Drawing Sheets

Specification includes a Sequence Listing.

(56) References Cited

OTHER PUBLICATIONS

Heidebrecht et al: Biomimetic fibers made of recombinant spidroins with the same toughness as natural spider silk. Adv. Mater, 2015, vol. 27, pp. 2189-2194.
Heim et al: Spider silk: from soluble to extraordinary fiber. Angewandte Chemie International Edition, May 4, 2009, vol. 48, No. 20, pp. 3584-3596.
Kinahan et al: Tunable Silk: Using Microfluidics to Fabricate Silk Fibers with Controllable Properties. Biomacromolecules, 2011 vol. 12, pp. 1504-1511.
Lang et al: Air filter devices including nonwoven meshes of electrospun recombinant spider silk proteins. J. Vis. Exp., 2013, vol. 4, e50492.
Lin et al: Predictive modelling-based design and experiments for synthesis and spinning of bioinspired silk fibres. Nat. Commun., 2015, vol. 6, pp. 1-12.
Meirovitch et al: Spider silk-CBD-Cellulose nanocrystal composites: mechanism of assembly. Intern. Journal of Moleculas Sciences, Sep. 18, 2016, vol. 17, No. 9.
Nudelman et al: Forming nacreous layer of the shells of the bivalves Atrina rigida and Pinctada margaritifera: An environmental- and cryo-scanning electron microscopy study. J. Struct. Biol., 2008, vol. 162, pp. 290-300.
Pereira et al: Silk-based biomaterials fuctionalized with fibronectin type II promotes cell adhesion. Acta Biomaterialia, Oct. 3, 2016, vol. 47, pp. 50-59.
Rammensee et al: Assembly mechanism of recombinant spider silk proteins. Proc. Natl. Acad. Sci. U.S.A., 2008, vol. 105, pp. 6590-6595.
Rising et al: Toward spinning artificial spider silk. Nat. Chem. Biol., 2015, vol. 11, pp. 309-315.
Teulé et al: A protocol for the production of recombinant spider silk-like proteins for artificial fiber spinning. Nat. Protoc., 2009, vol. 4, pp. 341-355.
Teulé et al: Combining flagelliform and dragline spider silk motifs to produce tunable synthetic biopolymer fibers. Biopolymers, 2012, vol. 97, pp. 418-431.
Tremblay et al: Spider wrapping silk fibre architecture arising from its modular soluble protein precursor. Sci. Rep., 2015, vol. 5, p. 11502.
Wong et al: Novel nanocomposites from spider silk-silica fusion (chimeric) proteins. Proc. Natl. Acad. Sci. U.S.A., 2006, vol. 103, pp. 9428-9433.
Xia et al: Native-sized recombinant spider silk protein produced in metabolically engineered *Escherichia coli* results in a strong fiber. Proc. Natl. Acad. Sci. U.S.A., 2010, vol. 107, pp. 14059-14063.

\* cited by examiner

SEQUENCE LISTING

```
<160> NUMBER OF SEQ ID NOS: 23

<210> SEQ ID NO 1
<211> LENGTH: 24
<212> TYPE: PRT
<213> ORGANISM: Artificial Sequence
<220> FEATURE:
<223> OTHER INFORMATION: Block A

<400> SEQUENCE: 1

Gly Pro Tyr Gly Pro Gly Ala Ser Ala Ala Ala Ala Ala Ala Gly Gly
1               5                   10                  15

Tyr Gly Pro Gly Ser Gly Gln Gln
            20
```

```
<210> SEQ ID NO 2
<211> LENGTH: 20
<212> TYPE: PRT
<213> ORGANISM: Artificial Sequence
<220> FEATURE:
<223> OTHER INFORMATION: Block Q

<400> SEQUENCE: 2

Gly Pro Gly Gln Gln Gly Pro Gly Gln Gln Gly Pro Gly Gln Gln Gly
1               5                   10                  15

Pro Gly Gln Gln
            20

<210> SEQ ID NO 3
<211> LENGTH: 499
<212> TYPE: PRT
<213> ORGANISM: Araneus diadematus
<220> FEATURE:
<223> OTHER INFORMATION: ADF3

<400> SEQUENCE: 3

Gly Pro Gly Gln Gln Gly Pro Gly Gln Gln Gly Pro Gly Gln Gln Gly
1               5                   10                  15

Pro Tyr Gly Pro Gly Ala Ser Ala Ala Ala Ala Ala Ala Gly Gly Tyr
            20                  25                  30

Gly Pro Gly Ser Gly Gln Gln Gly Pro Ser Gln Gln Gly Pro Gly Gln
        35                  40                  45

Gln Gly Pro Gly Gly Gln Gly Pro Tyr Gly Pro Gly Ala Ser Ala Ala
    50                  55                  60

Ala Ala Ala Ala Gly Gly Tyr Gly Pro Gly Ser Gly Gln Gln Gly Pro
65                  70                  75                  80

Gly Gly Gln Gly Pro Tyr Gly Pro Gly Ser Ser Ala Ala Ala Ala Ala
                85                  90                  95

Ala Gly Gly Asn Gly Pro Gly Ser Gln Gln Gly Ala Gly Gln Gln
            100                 105                 110

Gly Pro Gly Gln Gln Gly Pro Gly Gly Ser Ala Ala Ala Ala Ala Ala
        115                 120                 125

Gly Gly Tyr Gly Pro Gly Ser Gly Gln Gln Gly Pro Gly Gln Gln Gly
    130                 135                 140

Pro Gly Gln Gly Pro Tyr Gly Pro Gly Ala Ser Ala Ala Ala Ala
145                 150                 155                 160

Ala Ala Gly Gly Tyr Gly Pro Gly Ser Gly Gln Gly Pro Gly Gln Gln
                165                 170                 175

Gly Pro Gly Gly Gln Gly Pro Tyr Gly Pro Gly Ala Ser Ala Ala Ala
            180                 185                 190

Ala Ala Ala Gly Gly Tyr Gly Pro Gly Ser Gly Gln Gln Gly Pro Gly
        195                 200                 205

Gln Gln Gly Pro Gly Gln Gln Gly Pro Gly Gln Gly Pro Tyr Gly
    210                 215                 220

Pro Gly Ala Ser Ala Ala Ala Ala Ala Ala Gly Gly Tyr Gly Pro Gly
225                 230                 235                 240

Tyr Gly Gln Gln Gly Pro Gly Gln Gln Gly Pro Gly Gln Gly Pro
                245                 250                 255

Tyr Gly Pro Gly Ala Ser Ala Ala Ser Ala Ala Ser Gly Gly Tyr Gly
            260                 265                 270

Pro Gly Ser Gly Gln Gln Gly Pro Gly Gln Gln Gly Pro Gly Gly Gln
        275                 280                 285
```

-continued

Gly Pro Tyr Gly Pro Gly Ala Ser Ala Ala Ala Ala Gly Gly
    290             295                 300

Tyr Gly Pro Gly Ser Gly Gln Gln Gly Pro Gln Gln Gly Pro Gly
305                 310                 315                 320

Gln Gln Gly Pro Gly Gln Gln Gly Pro Gly Gln Gln Gly Pro Tyr Gly
                325                 330                 335

Pro Gly Ala Ser Ala Ala Ala Ala Ala Gly Gly Tyr Gly Pro Gly
            340                 345                 350

Ser Gly Gln Gln Gly Pro Gly Gln Gln Gly Pro Gly Gln Gln Gly Pro
    355                 360                 365

Gly Gln Gln Gly Pro Gly Gln Gln Gly Pro Gly Gln Gln Gly Pro Gly
370                 375                 380

Gln Gln Gly Pro Gly Gln Gln Gly Pro Gly Gln Gln Gly Pro Gly Gly
385                 390                 395                 400

Gln Gly Ala Tyr Gly Pro Gly Ala Ser Ala Ala Gly Ala Ala Gly
            405                 410                 415

Gly Tyr Gly Pro Gly Ser Gly Gln Gln Gly Pro Gly Gln Gln Gly Pro
        420                 425                 430

Gly Gln Gln Gly Pro Gly Gln Gln Gly Pro Gly Gln Gln Gly Pro Gly
    435                 440                 445

Gln Gln Gly Pro Gly Gln Gln Gly Pro Gly Gln Gln Gly Pro Tyr Gly
450                 455                 460

Pro Gly Ala Ser Ala Ala Ala Ala Ala Gly Gly Tyr Gly Pro Gly
465                 470                 475                 480

Ser Gly Gln Gln Gly Pro Gly Gln Gln Gly Pro Gly Gln Gln Gly Pro
        485                 490                 495

Gly Gly Gln

<210> SEQ ID NO 4
<211> LENGTH: 396
<212> TYPE: PRT
<213> ORGANISM: Latrodectus hesperus
<220> FEATURE:
<223> OTHER INFORMATION: AcSp1

<400> SEQUENCE: 4

Phe Gly Gly Pro Ser Ala Gly Gly Asp Val Ala Ala Lys Leu Ala Arg
1               5                   10                  15

Ser Leu Ala Ser Thr Leu Ala Ser Ser Gly Val Phe Arg Ala Ala Phe
            20                  25                  30

Asn Ser Arg Val Ser Thr Pro Val Ala Val Gln Leu Thr Asp Ala Leu
        35                  40                  45

Val Gln L

```
            145                 150                 155                 160
    Ile Thr Ala Glu Gly Pro Asp Phe Gly Ala Gly Tyr Pro Gly Gly Ala
                    165                 170                 175

Pro Thr Asp Leu Ser Gly Leu Asp Met Gly Ala Pro Ser Asp Gly Ser
                    180                 185                 190

Arg Gly Gly Asp Ala Thr Ala Lys Leu Leu Gln Ala Leu Val Pro Ala
                    195                 200                 205

Leu Leu Lys Ser Asp Val Phe Arg Ala Ile Tyr Lys Arg Gly Thr Arg
                    210                 215                 220

Lys Gln Val Val Gln Tyr Val Thr Asn Ser Ala Leu Gln Gln Ala Ala
    225                 230                 235                 240

Ser Ser Leu Gly Leu Asp Ala Ser Thr Ile Ser Gln Leu Gln Thr Lys
                    245                 250                 255

Ala Thr Gln Ala Leu Ser Ser Val Ser Ala Asp Ser Asp Ser Thr Ala
                    260                 265                 270

Tyr Ala Lys Ala Phe Gly Leu Ala Ile Ala Gln Val Leu Gly Thr Ser
                    275                 280                 285

Gly Gln Val Asn Asp Ala Asn Val Asn Gln Ile Gly Ala Lys Leu Ala
                    290                 295                 300

Thr Gly Ile Leu Arg Gly Ser Ser Ala Val Ala Pro Arg Leu Gly Ile
    305                 310                 315                 320

Asp Leu Ser Gly Ile Asn Val Asp Ser Asp Ile Gly Ser Val Thr Ser
                    325                 330                 335

Leu Ile Leu Ser Gly Ser Thr Leu Gln Met Thr Ile Pro Ala Gly Gly
                    340                 345                 350

Asp Asp Leu Ser Gly Gly Tyr Pro Gly Gly Phe Pro Ala Gly Ala Gln
                    355                 360                 365

Pro Ser Gly Gly Ala Pro Val Asp Ser Asn Ile Gly Leu Val Gly Thr
                    370                 375                 380

Gln Asp Val Ala Ile Gly Val Ser Gln Pro Val Asp
    385                 390                 395

<210> SEQ ID NO 5
<211> LENGTH: 23
<212> TYPE: PRT
<213> ORGANISM: Artificial Sequence
<220> FEATURE:
<223> OTHER INFORMATION: Linker N

<400> SEQUENCE: 5

Pro Ser Ala Ser Ala Ser Ala Ser Ala Gly Ser Ala Ala Ala Ser
1               5                   10                  15

Ala Gly Ala Gly Ala Gly Ala
            20

<210> SEQ ID NO 6
<211> LENGTH: 20
<212> TYPE: PRT
<213> ORGANISM: Artificial Sequence
<220> FEATURE:
<223> OTHER INFORMATION: Linker C

<400> SEQUENCE: 6

Ala Ser Ala Ser Ala Ser Ala Ala Ala Ser Ala Ala Ser Thr Val Ala
1               5                   10                  15

Asn Ser Ser Ser
            20
```

<210> SEQ ID NO 7
<211> LENGTH: 154
<212> TYPE: PRT
<213> ORGANISM: Clostridium thermocellum
<220> FEATURE:
<223> OTHER INFORMATION: CBM

<400> SEQUENCE: 7

| | | | | | | | | | | | | | | |
|---|---|---|---|---|---|---|---|---|---|---|---|---|---|---|
| Asn | Leu | Lys | Val | Glu | Phe | Tyr | Asn | Ser | Asn | Pro | Ser | Asp | Thr | Thr | Asn |
| 1 | | | | 5 | | | | | 10 | | | | | 15 | |
| Ser | Ile | Asn | Pro | Gln | Phe | Lys | Val | Thr | Asn | Thr | Gly | Ser | Ser | Ala | Ile |
| | | | 20 | | | | | 25 | | | | | 30 | | |
| Asp | Leu | Ser | Lys | Leu | Thr | Leu | Arg | Tyr | Tyr | Tyr | Thr | Val | Asp | Gly | Gln |
| | | | 35 | | | | | 40 | | | | | 45 | | |
| Lys | Asp | Gln | Thr | Phe | Trp | Cys | Asp | His | Ala | Ala | Ile | Ile | Gly | Ser | Asn |
| | 50 | | | | | 55 | | | | | 60 | | | | |
| Gly | Ser | Tyr | Asn | Gly | Ile | Thr | Ser | Asn | Val | Lys | Gly | Thr | Phe | Val | Lys |
| 65 | | | | | 70 | | | | | 75 | | | | | 80 |
| Met | Ser | Ser | Thr | Asn | Asn | Ala | Asp | Thr | Tyr | Leu | Glu | Ile | Ser | Phe |
| | | | | 85 | | | | | 90 | | | | | 95 | |
| Thr | Gly | Gly | Thr | Leu | Glu | Pro | Gly | Ala | His | Val | Gln | Ile | Gln | Gly | Arg |
| | | | 100 | | | | | 105 | | | | | 110 | | |
| Phe | Ala | Lys | Asn | Asp | Trp | Ser | Asn | Tyr | Thr | Gln | Ser | Asn | Asp | Tyr | Ser |
| | | | 115 | | | | | 120 | | | | | 125 | | |
| Phe | Lys | Ser | Ala | Ser | Gln | Phe | Val | Glu | Trp | Asp | Gln | Val | Thr | Ala | Tyr |
| | 130 | | | | | 135 | | | | | 140 | | | | |
| Leu | Asn | Gly | Val | Leu | Val | Trp | Gly | Lys | Glu |
| 145 | | | | | 150 | | | | | |

<210> SEQ ID NO 8
<211> LENGTH: 860
<212> TYPE: PRT
<213> ORGANISM: Artificial Sequence
<220> FEATURE:
<223> OTHER INFORMATION: CBM-L_N-AQ12-L_C-CBM-H6 fusion protein

<400> SEQUENCE: 8

| | | | | | | | | | | | | | | |
|---|---|---|---|---|---|---|---|---|---|---|---|---|---|---|---|
| Met | Gly | Asn | Leu | Lys | Val | Glu | Phe | Tyr | Asn | Ser | Asn | Pro | Ser | Asp | Thr |
| 1 | | | | 5 | | | | | 10 | | | | | 15 | |
| Thr | Asn | Ser | Ile | Asn | Pro | Gln | Phe | Lys | Val | Thr | Asn | Thr | Gly | Ser | Ser |
| | | | 20 | | | | | 25 | | | | | 30 | | |
| Ala | Ile | Asp | Leu | Ser | Lys | Leu | Thr | Leu | Arg | Tyr | Tyr | Tyr | Thr | Val | Asp |
| | | | 35 | | | | | 40 | | | | | 45 | | |
| Gly | Gln | Lys | Asp | Gln | Thr | Phe | Trp | Cys | Asp | His | Ala | Ala | Ile | Ile | Gly |
| | 50 | | | | | 55 | | | | | 60 | | | | |
| Ser | Asn | Gly | Ser | Tyr | Asn | Gly | Ile | Thr | Ser | Asn | Val | Lys | Gly | Thr | Phe |
| 65 | | | | | 70 | | | | | 75 | | | | | 80 |
| Val | Lys | Met | Ser | Ser | Thr | Asn | Asn | Ala | Asp | Thr | Tyr | Leu | Glu | Ile |
| | | | | 85 | | | | | 90 | | | | | 95 | |
| Ser | Phe | Thr | Gly | Gly | Thr | Leu | Glu | Pro | Gly | Ala | His | Val | Gln | Ile | Gln |
| | | | 100 | | | | | 105 | | | | | 110 | | |
| Gly | Arg | Phe | Ala | Lys | Asn | Asp | Trp | Ser | Asn | Tyr | Thr | Gln | Ser | Asn | Asp |
| | | | 115 | | | | | 120 | | | | | 125 | | |
| Tyr | Ser | Phe | Lys | Ser | Ala | Ser | Gln | Phe | Val | Glu | Trp | Asp | Gln | Val | Thr |
| | 130 | | | | | 135 | | | | | 140 | | | | |
| Ala | Tyr | Leu | Asn | Gly | Val | Leu | Val | Trp | Gly | Lys | Glu | Pro | Ser | Ala | Ser |
| 145 | | | | | 150 | | | | | 155 | | | | | 160 |

Ala Ser Ala Ser Ala Gly Ala Ser Ala Ala Ser Ala Gly Ala Gly
            165                 170                 175

Ala Gly Ala Gly Pro Gly Gln Gln Gly Pro Gly Gln Gln Gly Pro Gly
            180                 185                 190

Gln Gln Gly Pro Tyr Gly Pro Gly Ala Ser Ala Ala Ala Ala Ala
        195                 200                 205

Gly Gly Tyr Gly Pro Gly Ser Gly Gln Gln Gly Pro Ser Gln Gln Gly
        210                 215                 220

Pro Gly Gln Gln Gly Pro Gly Gly Gln Gly Pro Tyr Gly Pro Gly Ala
225                 230                 235                 240

Ser Ala Ala Ala Ala Ala Gly Gly Tyr Gly Pro Gly Ser Gly Gln
            245                 250                 255

Gln Gly Pro Gly Gly Gln Gly Pro Tyr Gly Pro Gly Ser Ser Ala Ala
            260                 265                 270

Ala Ala Ala Ala Gly Gly Asn Gly Pro Gly Ser Gly Gln Gln Gly Ala
        275                 280                 285

Gly Gln Gln Gly Pro Gly Gln Gln Gly Pro Gly Gly Ser Ala Ala Ala
            290                 295                 300

Ala Ala Ala Gly Gly Tyr Gly Pro Gly Ser Gly Gln Gln Gly Pro Gly
305                 310                 315                 320

Gln Gln Gly Pro Gly Gly Gln Gly Pro Tyr Gly Pro Gly Ala Ser Ala
            325                 330                 335

Ala Ala Ala Ala Gly Gly Tyr Gly Pro Gly Ser Gly Gln Gly Pro
        340                 345                 350

Gly Gln Gln Gly Pro Gly Gly Gln Gly Pro Tyr Gly Pro Gly Ala Ser
            355                 360                 365

Ala Ala Ala Ala Ala Gly Gly Tyr Gly Pro Gly Ser Gly Gln Gln
        370                 375                 380

Gly Pro Gly Gln Gln Gly Pro Gly Gln Gln Gly Pro Gly Gln Gly
385                 390                 395                 400

Pro Tyr Gly Pro Gly Ala Ser Ala Ala Ala Ala Ala Gly Gly Tyr
            405                 410                 415

Gly Pro Gly Tyr Gly Gln Gln Gly Pro Gly Gln Gln Gly Pro Gly Gly
            420                 425                 430

Gln Gly Pro Tyr Gly Pro Gly Ala Ser Ala Ala Ser Ala Ala Ser Gly
            435                 440                 445

Gly Tyr Gly Pro Gly Ser Gly Gln Gln Gly Pro Gly Gln Gln Gly Pro
        450                 455                 460

Gly Gly Gln Gly Pro Tyr Gly Pro Gly Ala Ser Ala Ala Ala Ala Ala
465                 470                 475                 480

Ala Gly Gly Tyr Gly Pro Gly Ser Gly Gln Gln Gly Pro Gly Gln Gln
            485                 490                 495

Gly Pro Gly Gln Gln Gly Pro Gly Gln Gln Gly Pro Gly Gln Gly
            500                 505                 510

Pro Tyr Gly Pro Gly Ala Ser Ala Ala Ala Ala Ala Gly Gly Tyr
            515                 520                 525

Gly Pro Gly Ser Gly Gln Gln Gly Pro Gly Gln Gln Gly Pro Gly Gln
            530                 535                 540

Gln Gly Pro Gly Gln Gln Gly Pro Gly Gln Gln Gly Pro Gly Gln Gln
545                 550                 555                 560

Gly Pro Gly Gln Gln Gly Pro Gly Gln Gln Gly Pro Gly Gln Gln Gly
            565                 570                 575

```
Pro Gly Gly Gln Gly Ala Tyr Gly Pro Gly Ala Ser Ala Ala Ala Gly
            580                 585                 590
Ala Ala Gly Gly Tyr Gly Pro Gly Ser Gly Gln Gln Gly Pro Gly Gln
        595                 600                 605
Gln Gly Pro Gly Gln Gln Gly Pro Gly Gln Gln Gly Pro Gly Gln Gln
    610                 615                 620
Gly Pro Gly Gln Gln Gly Pro Gly Gln Gln Gly Pro Gly Gln Gln Gly
625                 630                 635                 640
Pro Tyr Gly Pro Gly Ala Ser Ala Ala Ala Ala Ala Gly Gly Tyr
                645                 650                 655
Gly Pro Gly Ser Gly Gln Gln Gly Pro Gly Gln Gln Gly Pro Gly Gln
            660                 665                 670
Gln Gly Pro Gly Gly Gln Ala Ser Ala Ser Ala Ser Ala Ala Ala Ser
        675                 680                 685
Ala Ala Ser Thr Val Ala Asn Ser Ser Asn Leu Lys Val Glu Phe
    690                 695                 700
Tyr Asn Ser Asn Pro Ser Asp Thr Thr Asn Ser Ile Asn Pro Gln Phe
705                 710                 715                 720
Lys Val Thr Asn Thr Gly Ser Ser Ala Ile Asp Leu Ser Lys Leu Thr
                725                 730                 735
Leu Arg Tyr Tyr Tyr Thr Val Asp Gly Gln Lys Asp Gln Thr Phe Trp
            740                 745                 750
Cys Asp His Ala Ala Ile Ile Gly Ser Asn Gly Ser Tyr Asn Gly Ile
        755                 760                 765
Thr Ser Asn Val Lys Gly Thr Phe Val Lys Met Ser Ser Ser Thr Asn
    770                 775                 780
Asn Ala Asp Thr Tyr Leu Glu Ile Ser Phe Thr Gly Gly Thr Leu Glu
785                 790                 795                 800
Pro Gly Ala His Val Gln Ile Gln Gly Arg Phe Ala Lys Asn Asp Trp
                805                 810                 815
Ser Asn Tyr Thr Gln Ser Asn Asp Tyr Ser Phe Lys Ser Ala Ser Gln
            820                 825                 830
Phe Val Glu Trp Asp Gln Val Thr Ala Tyr Leu Asn Gly Val Leu Val
        835                 840                 845
Trp Gly Lys Glu Leu Glu His His His His His
    850                 855                 860

<210> SEQ ID NO 9
<211> LENGTH: 860
<212> TYPE: PRT
<213> ORGANISM: Artificial Sequence
<220> FEATURE:
<223> OTHER INFORMATION: CBM-L_N-Nat.AQ12-L_C-CBM-H6 fusion protein

<400> SEQUENCE: 9

Met Gly Asn Leu Lys Val Glu Phe Tyr Asn Ser Asn Pro Ser Asp Thr
1               5                   10                  15
Thr Asn Ser Ile Asn Pro Gln Phe Lys Val Thr Asn Thr Gly Ser Ser
            20                  25                  30
Ala Ile Asp Leu Ser Lys Leu Thr Leu Arg Tyr Tyr Tyr Thr Val Asp
        35                  40                  45
Gly Gln Lys Asp Gln Thr Phe Trp Cys Asp His Ala Ala Ile Ile Gly
    50                  55                  60
Ser Asn Gly Ser Tyr Asn Gly Ile Thr Ser Asn Val Lys Gly Thr Phe
65                  70                  75                  80
```

```
Val Lys Met Ser Ser Ser Thr Asn Asn Ala Asp Thr Tyr Leu Glu Ile
                85                  90                  95

Ser Phe Thr Gly Gly Thr Leu Glu Pro Gly Ala His Val Gln Ile Gln
            100                 105                 110

Gly Arg Phe Ala Lys Asn Asp Trp Ser Asn Tyr Thr Gln Ser Asn Asp
                115                 120                 125

Tyr Ser Phe Lys Ser Ala Ser Gln Phe Val Glu Trp Asp Gln Val Thr
        130                 135                 140

Ala Tyr Leu Asn Gly Val Leu Val Trp Gly Lys Glu Pro Ser Ala Ser
145                 150                 155                 160

Ala Ser Ala Ser Ala Gly Ala Ser Ala Ala Ser Ala Gly Ala Gly
                165                 170                 175

Ala Gly Ala Gly Pro Gly Gln Gln Gly Pro Gly Gln Gln Gly Pro Gly
            180                 185                 190

Gln Gln Gly Pro Tyr Gly Pro Gly Ala Ser Ala Ala Ala Ala Ala
            195                 200                 205

Gly Gly Tyr Gly Pro Gly Ser Gly Gln Gln Gly Pro Ser Gln Gln Gly
        210                 215                 220

Pro Gly Gln Gln Gly Pro Gly Gln Gln Gly Pro Tyr Gly Pro Gly Ala
225                 230                 235                 240

Ser Ala Ala Ala Ala Ala Gly Gly Tyr Gly Pro Gly Ser Gly Gln
                245                 250                 255

Gln Gly Pro Gly Gly Gln Gly Pro Tyr Gly Pro Gly Ser Ser Ala Ala
            260                 265                 270

Ala Ala Ala Ala Gly Gly Asn Gly Pro Gly Ser Gly Gln Gln Gly Ala
        275                 280                 285

Gly Gln Gln Gly Pro Gly Gln Gln Gly Pro Gly Gly Ser Ala Ala Ala
        290                 295                 300

Ala Ala Ala Gly Gly Tyr Gly Pro Gly Ser Gly Gln Gln Gly Pro Gly
305                 310                 315                 320

Gln Gln Gly Pro Gly Gly Gln Gly Pro Tyr Gly Pro Gly Ala Ser Ala
            325                 330                 335

Ala Ala Ala Ala Ala Gly Gly Tyr Gly Pro Gly Ser Gly Gln Gly Pro
            340                 345                 350

Gly Gln Gln Gly Pro Gly Gly Gln Gly Pro Tyr Gly Pro Gly Ala Ser
        355                 360                 365

Ala Ala Ala Ala Ala Gly Gly Tyr Gly Pro Gly Ser Gly Gln Gln
370                 375                 380

Gly Pro Gly Gln Gln Gly Pro Gly Gln Gln Gly Pro Gly Gly Gln Gly
385                 390                 395                 400

Pro Tyr Gly Pro Gly Ala Ser Ala Ala Ala Ala Ala Ala Gly Gly Tyr
            405                 410                 415

Gly Pro Gly Tyr Gly Gln Gln Gly Pro Gly Gln Gln Gly Pro Gly Gly
        420                 425                 430

Gln Gly Pro Tyr Gly Pro Gly Ala Ser Ala Ala Ser Ala Ala Ser Gly
        435                 440                 445

Gly Tyr Gly Pro Gly Ser Gly Gln Gln Gly Pro Gly Gln Gln Gly Pro
450                 455                 460

Gly Gly Gln Gly Pro Tyr Gly Pro Gly Ala Ser Ala Ala Ala Ala Ala
465                 470                 475                 480

Ala Gly Gly Tyr Gly Pro Gly Ser Gly Gln Gln Gly Pro Gly Gln Gln
        485                 490                 495

Gly Pro Gly Gln Gln Gly Pro Gly Gln Gln Gly Pro Gly Gly Gln Gly
```

```
            500                 505                 510
Pro Tyr Gly Pro Gly Ala Ser Ala Ala Ala Ala Ala Gly Gly Tyr
            515                 520                 525
Gly

-continued

```
1               5                   10                  15
Thr Asn Ser Ile Asn Pro Gln Phe Lys Val Thr Asn Thr Gly Ser Ser
                20                  25                  30
Ala Ile Asp Leu Ser Lys Leu Thr Leu Arg Tyr Tyr Tyr Thr Val Asp
                35                  40                  45
Gly Gln Lys Asp Gln Thr Phe Trp Cys Asp His Ala Ile Ile Gly
                50                  55                  60
Ser Asn Gly Ser Tyr Asn Gly Ile Thr Ser Asn Val Lys Gly Thr Phe
65                  70                  75                  80
Val Lys Met Ser Ser Thr Asn Asn Ala Asp Thr Tyr Leu Glu Ile
                85                  90                  95
Ser Phe Thr Gly Gly Thr Leu Glu Pro Gly Ala His Val Gln Ile Gln
                100                 105                 110
Gly Arg Phe Ala Lys Asn Asp Trp Ser Asn Tyr Thr Gln Ser Asn Asp
                115                 120                 125
Tyr Ser Phe Lys Ser Ala Ser Gln Phe Val Glu Trp Asp Gln Val Thr
130                 135                 140
Ala Tyr Leu Asn Gly Val Leu Val Trp Gly Lys Glu Pro Ser Ala Ser
145                 150                 155                 160
Ala Ser Ala Ser Ala Gly Ala Ser Ala Ala Ser Ala Gly Ala Gly
                165                 170                 175
Ala Gly Ala Phe Gly Gly Pro Ser Ala Gly Gly Asp Val Ala Ala Lys
                180                 185                 190
Leu Ala Arg Ser Leu Ala Ser Thr Leu Ala Ser Ser Gly Val Phe Arg
                195                 200                 205
Ala Ala Phe Asn Ser Arg Val Ser Thr Pro Val Ala Val Gln Leu Thr
                210                 215                 220
Asp Ala Leu Val Gln Lys Ile Ala Ser Asn Leu Gly Leu Asp Tyr Ala
225                 230                 235                 240
Thr Ala Ser Lys Leu Arg Lys Ala Ser Gln Ala Val Ser Lys Val Arg
                245                 250                 255
Met Gly Ser Asp Thr Asn Ala Tyr Ala Leu Ala Ile Ser Ser Ala Leu
                260                 265                 270
Ala Glu Val Leu Ser Ser Ser Gly Lys Val Ala Asp Ala Asn Ile Asn
                275                 280                 285
Gln Ile Ala Pro Gln Leu Ala Ser Gly Ile Val Leu Gly Val Ser Thr
                290                 295                 300
Thr Ala Pro Gln Phe Gly Val Asp Leu Ser Ser Ile Asn Val Asn Leu
305                 310                 315                 320
Asp Ile Ser Asn Val Ala Arg Asn Met Gln Ala Ser Ile Gln Gly Gly
                325                 330                 335
Pro Ala Pro Ile Thr Ala Glu Gly Pro Asp Phe Gly Ala Gly Tyr Pro
                340                 345                 350
Gly Gly Ala Pro Thr Asp Leu Ser Gly Leu Asp Met Gly Ala Pro Ser
                355                 360                 365
Asp Gly Ser Arg Gly Gly Asp Ala Thr Ala Lys Leu Leu Gln Ala Leu
                370                 375                 380
Val Pro Ala Leu Leu Lys Ser Asp Val Phe Arg Ala Ile Tyr Lys Arg
385                 390                 395                 400
Gly Thr Arg Lys Gln Val Val Gln Tyr Val Thr Asn Ser Ala Leu Gln
                405                 410                 415
Gln Ala Ala Ser Ser Leu Gly Leu Asp Ala Ser Thr Ile Ser Gln Leu
                420                 425                 430
```

```
Gln Thr Lys Ala Thr Gln Ala Leu Ser Ser Val Ser Ala Asp Ser Asp
        435                 440                 445

Ser Thr Ala Tyr Ala Lys Ala Phe Gly Leu Ala Ile Ala Gln Val Leu
    450                 455                 460

Gly Thr Ser Gly Gln Val Asn Asp Ala Asn Val Asn Gln Ile Gly Ala
465                 470                 475                 480

Lys Leu Ala Thr Gly Ile Leu Arg Gly Ser Ala Val Ala Pro Arg
                485                 490                 495

Leu Gly Ile Asp Leu Ser Gly Ile Asn Val Asp Ser Asp Ile Gly Ser
                500                 505                 510

Val Thr Ser Leu Ile Leu Ser Gly Ser Thr Leu Gln Met Thr Ile Pro
        515                 520                 525

Ala Gly Gly Asp Asp Leu Ser Gly Gly Tyr Pro Gly Gly Phe Pro Ala
    530                 535                 540

Gly Ala Gln Pro Ser Gly Gly Ala Pro Val Asp Ser Asn Ile Gly Leu
545                 550                 555                 560

Val Gly Thr Gln Asp Val Ala Ile Gly Val Ser Gln Pro Val Asp Ala
                565                 570                 575

Ser Ala Ser Ala Ser Ala Ala Ser Ala Ala Ser Thr Val Ala Asn
        580                 585                 590

Ser Ser Ser Asn Leu Lys Val Glu Phe Tyr Asn Ser Asn Pro Ser Asp
    595                 600                 605

Thr Thr Asn Ser Ile Asn Pro Gln Phe Lys Val Thr Asn Thr Gly Ser
610                 615                 620

Ser Ala Ile Asp Leu Ser Lys Leu Thr Leu Arg Tyr Tyr Tyr Thr Val
625                 630                 635                 640

Asp Gly Gln Lys Asp Gln Thr Phe Trp Cys Asp His Ala Ala Ile Ile
                645                 650                 655

Gly Ser Asn Gly Ser Tyr Asn Gly Ile Thr Ser Asn Val Lys Gly Thr
                660                 665                 670

Phe Val Lys Met Ser Ser Ser Thr Asn Asn Ala Asp Thr Tyr Leu Glu
        675                 680                 685

Ile Ser Phe Thr Gly Gly Thr Leu Glu Pro Gly Ala His Val Gln Ile
    690                 695                 700

Gln Gly Arg Phe Ala Lys Asn Asp Trp Ser Asn Tyr Thr Gln Ser Asn
705                 710                 715                 720

Asp Tyr Ser Phe Lys Ser Ala Ser Gln Phe Val Glu Trp Asp Gln Val
                725                 730                 735

Thr Ala Tyr Leu Asn Gly Val Leu Val Trp Gly Lys Glu Leu Glu His
                740                 745                 750

His His His His His
        755

<210> SEQ ID NO 11
<211> LENGTH: 2580
<212> TYPE: DNA
<213> ORGANISM: Artificial Sequence
<220> FEATURE:
<223> OTHER INFORMATION: Nucleic acid sequence encoding fusion protein
      CBM-L_N-AQ12-L_C-CBM-H6

<400> SEQUENCE: 11
atgggcaatc tgaaagtgga gttctataat agcaatccga gcgataccac caatagcatt      60
aatccgcagt ttaaagttac caataccggt agcagcgcaa ttgatctgag caaactgacc     120
```

```
ctgcgttatt actataccgt tgatggtcag aaagatcaga cattttggtg tgatcatgca    180
gccattattg gtagcaatgg tagctataat ggcattacca gcaatgtgaa aggcaccttt    240
gttaaaatga gcagcagcac caataatgcc gatacctatc tggaaattag ctttaccggt    300
ggcacccctgg aaccgggtgc acatgttcag attcagggtc gttttgcaaa aaatgattgg    360
agcaattata cccagagcaa cgactatagc tttaaaagcg caagccagtt tgttgaatgg    420
gatcaggtta ccgcatatct gaatggtgtt ctggtttggg gtaaagaacc gagcgctagc    480
gcaagcgcat cagccggtgc aagtgctgca gcaagtgccg gtgctggtgc gggtgcaggt    540
cctggtcagc agggtccggg tcaacaagga cctggacagc aaggaccgta tggtccaggt    600
gcatcagctg cagccgcagc agcgggtggt tatggtccgg gaagcggtca gcaaggccct    660
tcacaacagg gaccaggcca acaggtcct ggcggtcaag gtccttatgg acctggtgct    720
tctgctgcgg cagcggctgc cggtggctat ggccctggta gtggccagca agggcctggt    780
ggccagggtc catatggccc aggttctagt gccgcagctg ctgctgcagg cggtaatgga    840
ccgggttcag acaacaagg tgcagggcag caaggtcccg acaacaggg tccaggtggt    900
agtgcagcag cggcagcagc tggcggatat ggaccaggta gtgggcaaca aggcccaggt    960
caacaagggc caggggtca aggcccatac ggtccgggtg cttccgcagc cgcagctgca    1020
gcaggcggtt acgtcctgg tagtggtcaa ggtccaggcc agcaaggacc aggtggacaa    1080
gggccttacg gaccaggcgc atctgcggca gcagcagccg caggggggata tggtcctggt    1140
tcagggcagc agggaccagg tcagcaaggt ccaggtcagc agggacctgg gggtcaggga    1200
ccttacggtc ctggcgcaag tgcagctgca gcggcagcgg gtggctacgg accgggttat    1260
ggccagcagg gaccgggaca gcagggaccc ggtggacagg gtccgtatgg accgggtgca    1320
agtgcagcat cagcagcaag tggtggttac ggacctggct caggacagca aggccctggc    1380
caacaaggcc ctggcggaca gggaccctat gggccaggtg ccagcgctgc agcagccgca    1440
gccggtggat acggtccagg ctctggtcaa caaggtcctg gcaacaagg tcctggccag    1500
cagggtccag gacagcaagg gcctggcggt caaggaccgt acggaccggg tgccagcgca    1560
gcggctgcag cggcaggcgg ttatggtcca ggatcaggcc agcaaggtcc gggtcagcaa    1620
ggcccagggc agcaaggacc gggtcaacag ggaccgggtc agcagggtcc tgggcaacag    1680
ggtccgggac aacagggacc aggtcaacaa ggaccgggtc aacaaggtcc aggtggtcag    1740
ggtgcatatg gtcctggcgc ttcagcagca gcaggggctg caggggggtta tggcccaggt    1800
agcggtcagc agggacccgg acaacaaggc cctggacaac agggtcccgg tcagcaaggg    1860
ccaggccaac aaggtccagg acaacaagga ccagggcagc agggtccagg ccaacaaggc    1920
ccttatggtc cgggtgccag tgctgcggca gcggcagctg ggggttatgg tccaggctct    1980
ggacagcagg gacctggcca gcaaggacct gggcagcaag ggccaggcgg tcaggcaagt    2040
gcatcagcaa gcgcagcagc gagtgcagca agcaccgttg cgaattctag ctccaacctg    2100
aaagttgagt tttataactc caatccgtca gatacgacga acagtattaa ccctcagttc    2160
aaagtgacaa acaccggttc aagcgccatc gatctgtcaa aactgacatt acgttactat    2220
tatacagtgg acgccagaa agaccaaacc ttctggtgcg accatgccgc aattatcggt    2280
tcaaatggtt catataacgg tatcacgagc aacgtcaaag gtacattcgt gaaaatgagt    2340
agctcaacca acaacgcaga tacctactta gaaatttcat ttacgggtgg tacgttagaa    2400
ccaggtgcgc acgtgcagat ccaaggtcgc ttcgccaaaa acgactggtc aaattataca    2460
cagtcgaatg actacagctt caaatcagca tcacagttcg tagagtggga tcaagtgaca    2520
```

```
gcctacctga acggcgtgct ggtgtggggc aaagaactcg agcaccacca ccaccaccac    2580
```

<210> SEQ ID NO 12
<211> LENGTH: 2580
<212> TYPE: DNA
<213> ORGANISM: Artificial Sequence
<220> FEATURE:
<223> OTHER INFORMATION: Nucleic acid sequence encoding fusion protein
      CBM-L_N-Nat.AQ12-L_C-CBM-H6

<400> SEQUENCE: 12

```
atgggcaatc tgaaagtgga gttctataat agcaatccga gcgataccac caatagcatt      60
aatccgcagt ttaaagttac caataccggt agcagcgcaa ttgatctgag caaactgacc     120
ctgcgttatt actataccgt tgatggtcag aaagatcaga cattttggtg tgatcatgca     180
gccattattg gtagcaatgg tagctataat ggcattacca gcaatgtgaa aggcaccttt     240
gttaaaatga gcagcagcac caataatgcc gataccctatc tggaaattag ctttaccggt    300
ggcaccctgg aaccgggtgc acatgttcag attcagggtc gttttgcaaa aaatgattgg    360
agcaattata cccagagcaa cgactatagc tttaaaagcg caagccagtt tgttgaatgg    420
gatcaggtta ccgcatatct gaatggtgtt ctggtttggg gtaaagaacc gagcgctagc    480
gcaagcgcat cagccggtgc aagtgctgca gcaagtgccg gtgctggtgc gggtgcaggt    540
cctggtcagc agggtccggg tcaacaagga cctggacagc aaggaccgta tggtccaggt    600
gcatcagctg cagccgcagc agcgggtggt tatggtccgg aagcggtca gcaaggccct    660 tcacaacagg gaccaggcca acagggtcct ggcggtcaag tccttatgg acctggtgct    720 tctgctgcgg cagcggctgc cggtggctat ggccctggta gtggccagca agggcctggt    780
ggccagggtc catatggccc aggttctagt gccgcagctg ctgctgcagg cggtaatgga    840
ccgggttcag acaacaaggt gcagggcag caaggtcccg acaacaggg tccaggtggt    900 agtgcagcag cggcagcagc tggcggatat ggaccaggta gtgggcaaca aggcccaggt    960 caacaaggc caggggtca aggcccatac ggtccgggtg cttccgcagc cgcagctgca   1020
gcaggcggtt acggtcctgg tagtggtcaa ggtccaggcc agcaaggacc aggtggacaa   1080
gggccttacg gaccaggcgc atctgcggca gcagcagccg caggggagata tggtcctggt   1140 tcagggcagc agggaccagg tcagcaaggt ccaggtcagc agggacctgg gggtcaggga   1200
ccttacggtc ctggcgcaag tgcagctgca gcggcagcgg tggctacgg accgggttat   1260 ggccagcagg gaccgggaca gcagggaccc ggtggacagg tccgtatgg accgggtgca   1320 agtgcagcat cagcagcaag tggtggttac ggacctggct caggacagca aggccctggc   1380
caacaaggcc ctggcggaca gggaccctat gggccaggtg ccagcgctgc agcagccgca   1440
gccggtggat acggtccagg ctctggtcaa caaggtcctg gcaacaagg tcctggccag   1500 cagggtccag acagcaagg gcctggcggt caaggaccgt acggaccggg tgccagcgca   1560
gcggctgcag cggcaggcgg ttatggtcca ggatcaggcc agcaaggtcc gggtcagcaa   1620
ggcccagggc agcaaggacc gggtcaacag ggaccgggtc agcagggtcc tgggcaacag   1680
ggtccgggac aacagggacc aggtcaacaa ggaccgggtc aacaaggtcc aggtggtcag   1740
ggtgcatatg gtcctggcgc ttcagcagca gcaggggctg caggggggtta tggcccaggt   1800 agcggtcagc agggacccgg acaacaaggc cctggacaac aggtgtccgg tcagcaaggg   1860
ccaggccaac aaggtccagg acaacaagga ccagggcagc agggtccagg ccaacaaggc   1920
ccttatggtc cgggtgccag tgctgcggca gcggcagctg ggggttatgg tccaggctct   1980
```

```
ggacagcagg gacctggcca gcaaggacct gggcagcaag ggccaggcgg tcaggcaagt    2040
gcatcagcaa gcgcagcagc gagtgcagca agcaccgttg cgaattctag ctccaacctg    2100
aaagttgagt tttataactc caatccgtca gatacgacga acagtattaa ccctcagttc    2160
aaagtgacaa acaccggttc aagcgccatc gatctgtcaa aactgacatt acgttactat    2220
tatacagtgg acggccagaa agaccaaacc ttctggtgcg accatgccgc aattatcggt    2280
tcaaatggtt catataacgg tatcacgagc aacgtcaaag gtacattcgt gaaaatgagt    2340
agctcaacca caacgcaga tacctactta gaaatttcat ttacgggtgg tacgttagaa    2400
ccaggtgcgc acgtgcagat ccaaggtcgc ttcgccaaaa acgactggtc aaattataca    2460
cagtcgaatg actacagctt caaatcagca tcacagttcg tagagtggga tcaagtgaca    2520
gcctacctga acggcgtgct ggtgtggggc aaagaactcg agcaccacca ccaccaccac    2580
```

<210> SEQ ID NO 13
<211> LENGTH: 2271
<212> TYPE: DNA
<213> ORGANISM: Artificial Sequence
<220> FEATURE:
<223> OTHER INFORMATION: Nucleic acid sequence encoding fusion protein
      CBM-L_N-L.hes.AcSp1-L_C-CBM-H6

<400> SEQUENCE: 13

```
atgggcaatc tgaaagtcga attttacaac agcaatccga gcgataccac gaacagcatc      60
aatccgcagt ttaaggttac gaacacgggc agctccgcaa ttgatctgtc aaaactgacc     120
ctgcgttatt actatacggt ggatggccag aaggaccaaa ccttttggtg cgaccatgcg     180
gccattatcg gctcgaacgg tagctacaat ggcatcacct cgaacgtcaa aggcacgttc     240
gtgaagatga gctctagtac caacaatgcc gatacgtatc tggaaattag ttttaccggc     300
ggtacgctgg aaccgggtgc acacgttcag atccaaggtc gcttcgctaa aaacgattgg     360
tctaattaca cccagtctaa cgactatagt tttaagtccg cgtcacagtt cgttgaatgg     420
gatcaagtca cggcctacct gaatggcgtg ctggtttggg gtaaagaacc gagcgcgagc     480
gcaagcgcaa gtgccggtgc aagcgcagca gcatcagccg tgctggtgca aggcgccttt     540
ggtggtccga gtgccggtgg tgatgttgca gcaaaactgg cacgtagcct ggcaagcacc     600
ctggcaagca gcgtgttttt cgtgcagca tttaatagcc gtgttagcac accggttgca     660
gttcagctga ccgatgcact ggttcagaaa attgcaagca tctgggtct ggattatgca     720 accgcaagca aactgcgtaa agcaagccag gcagttagca agttcgtat gggtagcgat     780 accaatgcat atgcactggc aattagcagc gcactggcag aagttctgag cagcagcggt     840
aaagttgcag atgcaaacat taatcagatt gcaccgcagc tggcaagcgg tattgttctg     900
ggtgttagca ccaccgcacc gcagtttggt gttgatctga gcagcattaa tgtgaacctg     960
gatattagca atgtggcacg taatatgcag gcaagcattc agggtggtcc ggcaccgatt    1020
acagccgaag gtccggattt tggtgcaggt tatccgggtg tgcaccgac cgatctgagc    1080 ggtctggata tgggtgcacc gagtgatggt agccgtggtg gtgatgcaac cgccaaactg    1140
ctgcaggcac tggttccggc actgctgaaa agtgatgtgt tcgtgcaat ctataaacgt    1200 ggcacccgta acaggttgt tcagtatgtt accaatagcg cactgcagca ggcagcaagc    1260
agcctgggcc tggatgcaag caccattagc cagctgcaga ccaaagcaac ccaggcactg    1320 agcagccgtta gcgcagatag cgatagcacc gcatatgcaa aagcatttgg tctggcaatt    1380
gcacaggttc tgggcaccag cggtcaggtt aatgatgcaa atgtgaatca gattggtgca    1440
```

-continued

```
aaactggcca ccggtattct gcgtggtagc agcgcagttg caccgcgtct gggtattgat    1500
ctgagtggta ttaatgtgga tagcgatatt ggtagcgtta ccagcctgat tctgagcggt    1560 agcacccctgc agatgaccat tccggcaggc ggtgatgatc tgtcaggtgg ctatccgggt   1620
ggctttcctg ccggtgcaca gccgagtggt ggcgcaccgg ttgatagcaa tattggtctg    1680
gttggcaccc aggatgttgc aattggtgtt agccagccgg ttgatgccag cgcaagcgca    1740
agtgcagcag caagcgcagc cagcaccgtt gcaaatagct ctagcaatct gaaagtcgaa    1800
ttttacaaca gcaatccgag cgataccacg aacagcatca atccgcagtt taaggttacg    1860
aacacgggca gctccgcaat tgatctgtca aaactgaccc tgcgttatta ctatacggtg    1920
gatggccaga aggaccaaac ctttggtgc gaccatgcgg ccattatcgg ctcgaacggt     1980
agctacaatg gcatcacctc gaacgtcaaa ggcacgttcg tgaagatgag ctctagtacc    2040
aacaatgccg atacgtatct ggaaattagt ttaccggcg gtacgctgga accgggtgca     2100
cacgttcaga tccaaggtcg cttcgctaaa acgattggt ctaattacac ccagtctaac     2160
gactatagtt ttaagtccgc gtcacagttc gttgaatggg atcaagtcac ggcctacctg    2220
aatggcgtgc tggtttgggg taaagaactc gagcaccacc accaccacca c             2271
```

<210> SEQ ID NO 14
<211> LENGTH: 116
<212> TYPE: PRT
<213> ORGANISM: Streptococcus pyogenes
<220> FEATURE:
<223> OTHER INFORMATION: SpyCatcher

<400> SEQUENCE: 14

```
Gly Ala Met Val Asp Thr Leu Ser Gly Leu Ser Ser Glu Gln Gly Gln
1               5                   10                  15

Ser Gly Asp Met Thr Ile Glu Glu Asp Ser Ala Thr His Ile Lys Phe
            20                  25                  30

Ser Lys Arg Asp Glu Asp Gly Lys Glu Leu Ala Gly Ala Thr Met Lys
        35                  40                  45

Leu Arg Asp Ser Ser Gly Lys Thr Ile Ser Thr Trp Ile Ser Asp Gly
    50                  55                  60

Gln Val Lys Asp Phe Tyr Leu Tyr Pro Gly Lys Tyr Thr Phe Val Glu
65                  70                  75                  80

Thr Ala Ala Pro Asp Gly Tyr Glu Val Ala Thr Ala Ile Thr Phe Thr
                85                  90                  95

Val Asn Glu Gln Gly Gln Val Thr Val Asn Gly Lys Ala Thr Lys Gly
            100                 105                 110

Asp Ala His Ile
        115
```

<210> SEQ ID NO 15
<211> LENGTH: 781
<212> TYPE: PRT
<213> ORGANISM: Artificial Sequence
<220> FEATURE:
<223> OTHER INFORMATION: SpyCatcher-L_ N-Nat.AQ12-L_C- SpyCatcher-H6

<400> SEQUENCE: 15

```
Met Gly Ala Met Val Asp Thr Leu Ser Gly Leu Ser Ser Glu Gln Gly
1               5                   10                  15

Gln Ser Gly Asp Met Thr Ile Glu Glu Asp Ser Ala Thr His Ile Lys
            20                  25                  30
```

```
Phe Ser Lys Arg Asp Glu Asp Gly Lys Glu Leu Ala Gly Ala Thr Met
            35                  40                  45
Lys Leu Arg Asp Ser Ser Gly Lys Thr Ile Ser Thr Trp Ile Ser Asp
 50                  55                  60
Gly Gln Val Lys Asp Phe Tyr Leu Tyr Pro Gly Lys Tyr Thr Phe Val
 65                  70                  75                   80
Glu Thr Ala Ala Pro Asp Gly Tyr Glu Val Ala Thr Ala Ile Thr Phe
                 85                  90                  95
Thr Val Asn Glu Gln Gly Gln Val Thr Val Asn Gly Lys Ala Thr Lys
            100                 105                 110
Gly Asp Ala His Ile Ser Ala Ser Ala Ser Ala Ser Ala Gly Ala Ser
            115                 120                 125
Ala Ala Ala Ser Ala Gly Ala Gly Ala Gly Ala Gly Pro Gly Gln Gln
        130                 135                 140
Gly Pro Gly Gln Gln Gly Pro Gly Gln Gln Gly Pro Tyr Gly Pro Gly
145                 150                 155                 160
Ala Ser Ala Ala Ala Ala Ala Gly Gly Tyr Gly Pro Gly Ser Gly
            165                 170                 175
Gln Gln Gly Pro Ser Gln Gln Gly Pro Gly Gln Gln Gly Pro Gly Gly
            180                 185                 190
Gln Gly Pro Tyr Gly Pro Gly Ala Ser Ala Ala Ala Ala Ala Gly
            195                 200                 205
Gly Tyr Gly Pro Gly Ser Gln Gln Gly Pro Gly Gln Gln Gly Pro
            210                 215                 220
Tyr Gly Pro Gly Ser Ser Ala Ala Ala Ala Ala Gly Gly Asn Gly
225                 230                 235                 240
Pro Gly Ser Gly Gln Gln Gly Ala Gly Gln Gln Gly Pro Gly Gln Gln
            245                 250                 255
Gly Pro Gly Gly Ser Ala Ala Ala Ala Ala Gly Gly Tyr Gly Pro
            260                 265                 270
Gly Ser Gly Gln Gln Gly Pro Gly Gln Gln Gly Pro Gly Gln Gly
            275                 280                 285
Pro Tyr Gly Pro Gly Ala Ser Ala Ala Ala Ala Ala Gly Gly Tyr
290                 295                 300
Gly Pro Gly Ser Gly Gln Gly Pro Gly Gln Gln Gly Pro Gly Gln
305                 310                 315                 320
Gly Pro Tyr Gly Pro Gly Ala Ser Ala Ala Ala Ala Ala Gly Gly
            325                 330                 335
Tyr Gly Pro Gly Ser Gln Gln Gly Pro Gly Gln Gln Gly Pro Gly
            340                 345                 350
Gln Gln Gly Pro Gly Gly Gln Gly Pro Tyr Gly Pro Gly Ala Ser Ala
            355                 360                 365
Ala Ala Ala Ala Gly Gly Tyr Gly Pro Gly Tyr Gly Gln Gln Gly
            370                 375                 380
Pro Gly Gln Gln Gly Pro Gly Gln Gly Pro Tyr Gly Pro Gly Ala
385                 390                 395                 400
Ser Ala Ala Ser Ala Ala Ser Gly Gly Tyr Gly Pro Gly Ser Gly Gln
                 405                 410                 415
Gln Gly Pro Gly Gln Gly Pro Gly Gly Gly Pro Tyr Gly Pro
            420                 425                 430
Gly Ala Ser Ala Ala Ala Ala Ala Gly Gly Tyr Gly Pro Gly Ser
            435                 440                 445
Gly Gln Gln Gly Pro Gly Gln Gln Gly Pro Gly Gln Gln Gly Pro Gly
```

```
                450             455             460
Gln Gln Gly Pro Gly Gly Gln Gly Pro Tyr Gly Pro Gly Ala Ser Ala
465                 470                 475                 480

Ala Ala Ala Ala Ala Gly Gly Tyr Gly Pro Gly Ser Gly Gln Gln Gly
                485                 490                 495

Pro Gly Gln Gln Gly Pro Gly Gln Gln Gly Pro Gly Gln Gln Gly Pro
            500                 505                 510

Gly Gln Gln Gly Pro Gly Gln Gln Gly Pro Gly Gln Gln Gly Pro Gly
        515                 520                 525

Gln Gln Gly Pro Gly Gln Gln Gly Pro Gly Gly Gln Gly Ala Tyr Gly
    530                 535                 540

Pro Gly Ala Ser Ala Ala Ala Gly Ala Ala Gly Gly Tyr Gly Pro Gly
545                 550                 555                 560

Ser Gly Gln Gln Gly Pro Gly Gln Gln Gly Pro Gly Gln Gln Gly Pro
                565                 570                 575

Gly Gln Gln Gly Pro Gly Gln Gln Gly Pro Gly Gln Gln Gly Pro Gly
            580                 585                 590

Gln Gln Gly Pro Gly Gln Gln Gly Pro Tyr Gly Pro Gly Ala Ser Ala
        595                 600                 605

Ala Ala Ala Ala Gly Gly Tyr Gly Pro Gly Ser Gly Gln Gln Gly
    610                 615                 620

Pro Gly Gln Gln Gly Pro Gly Gln Gln Gly Pro Gly Gly Gln Ala Ser
625                 630                 635                 640

Ala Ser Ala Ser Ala Ala Ala Ser Ala Ala Ser Thr Val Ala Asn Ser
                645                 650                 655

Ser Ser Ala Met Val Asp Thr Leu Ser Gly Leu Ser Ser Glu Gln Gly
            660                 665                 670

Gln Ser Gly Asp Met Thr Ile Glu Glu Asp Ser Ala Thr His Ile Lys
        675                 680                 685

Phe Ser Lys Arg Asp Glu Asp Gly Lys Glu Leu Ala Gly Ala Thr Met
690                 695                 700

Lys Leu Arg Asp Ser Ser Gly Lys Thr Ile Ser Thr Trp Ile Ser Asp
705                 710                 715                 720

Gly Gln Val Lys Asp Phe Tyr Leu Tyr Pro Gly Lys Tyr Thr Phe Val
                725                 730                 735

Glu Thr Ala Ala Pro Asp Gly Tyr Glu Val Ala Thr Ala Ile Thr Phe
            740                 745                 750

Thr Val Asn Glu Gln Gly Gln Val Thr Val Asn Gly Lys Ala Thr Lys
        755                 760                 765

Gly Asp Ala His Ile Leu Glu His His His His His His
770                 775                 780

<210> SEQ ID NO 16
<211> LENGTH: 2346
<212> TYPE: DNA
<213> ORGANISM: Artificial Sequence
<220> FEATURE:
<223> OTHER INFORMATION: SpyCatcher-L_ N-Nat.AQ12-L_C- SpyCatcher-H6

<400> SEQUENCE: 16
atgggcgcaa tggttgatac cctgagcggt ctgagcagcg aacagggtca gagcggtgat    60
atgaccattg aagaagatag cgcaacccac atcaaattca gcaaacgtga tgaagatggt   120
aaagaactgg caggcgcaac catgaaactg cgtgatagcg cggtaaaac cattagcacc    180 tggattagtg atggtcaggt gaaagatttt tatctgtacc ctggcaaata caccttgtt    240
```

```
gaaaccgcag caccggatgg ttatgaagtt gcaaccgcaa ttacctttac cgttaatgaa      300
cagggccagg ttaccgtgaa tggtaaagca accaaaggtg atgcacatat tagtgctagc      360
gcaagcgcat cagccggtgc aagtgctgca gcaagtgccg gtgctggtgc gggtgcaggt      420
cctggtcagc agggtccggg tcaacaagga cctggacagc aaggaccgta tggtccaggt      480
gcatcagctg cagccgcagc agcgggtggt tatggtccgg gaagcggtca gcaaggccct      540
tcacaacagg gaccaggcca acagggtcct ggcggtcaag gtccttatgg acctggtgct      600
tctgctgcgg cagcggctgc cggtggctat ggccctggta gtggccagca agggcctggt      660
ggccagggtc catatggccc aggttctagt gccgcagctg ctgctgcagg cggtaatgga      720
ccgggttcag acaacaagg tgcagggcag caaggtcccg acaacaggg tccaggtggt       780 agtgcagcag cggcagcagc tggcggatat ggaccaggta gtgggcaaca aggcccaggt      840
caacaagggc caggggtca aggcccatac ggtccgggtg cttccgcagc cgcagctgca       900
gcaggcggtt acgtcctgg tagtggtcaa ggtccaggcc agcaaggacc aggtggacaa       960
gggccttacg gaccaggcgc atctgcggca gcagcagccg cagggggata tggtcctggt     1020
tcagggcagc agggaccagg tcagcaaggt ccaggtcagc agggacctgg ggtcagggga     1080
ccttacggtc ctggcgcaag tgcagctgca gcggcagcgg tggctacgg accgggttat      1140 ggccagcagg gaccgggaca gcagggaccc ggtggacagg gtccgtatgg accgggtgca     1200
agtgcagcat cagcagcaag tggtggttac ggacctggct caggacagca aggccctggc     1260
caacaaggcc ctggcggaca gggaccctat gggccaggtg ccagcgctgc agcagccgca     1320
gccggtggat acgtccagg ctctggtcaa caaggtcctg gcaacaagg tcctggccag      1380 cagggtccag acagcaagg gcctggcggt caaggaccgt acggaccggg tgccagcgca     1440
gcggctgcag cggcaggcgg ttatggtcca ggatcaggcc agcaaggtcc gggtcagcaa     1500
ggcccagggc agcaaggacc gggtcaacag gaccgggtc agcagggtcc tgggcaacag     1560
ggtccgggac aacaggacc aggtcaacaa ggaccgggtc aacaaggtcc aggtggtcag     1620
ggtgcatatg gtcctggcgc ttcagcagca gcagggctg caggggtta tggcccaggt      1680 agcggtcagc agggacccgg acaacaaggc cctggacaac aggtcccgg tcagcaaggg      1740 ccaggccaac aagtccagg acaacaagga ccagggcagc agggtccagg ccaacaaggc      1800
ccttatggtc cggtgccag tgctgcgca gcggcagctg ggggtatg tccaggctct       1860 ggacagcagg gacctggcca gcaaggacct gggcagcaag gccaggcgg tcaggcaagt     1920 gcatcagcaa gcgcagcagc gagtgcagca agcaccgttg cgaattctag ctccgcaatg     1980 gttgatacc tgagcggtct gagcagcgaa caggtcaga gcggtgatat gaccattgaa       2040
gaagatagcg caacccacat caaattcagc aaacgtgatg aagatggtaa agaactggca     2100
ggcgcaacca tgaaactgcg tgatagcagc ggtaaaacca ttagcacctg gattagtgat     2160
ggtcaggtga agatttttta tctgtaccct ggcaaataca cctttgttga aaccgcagca     2220
ccggatggtt atgaagttgc aaccgcaatt acctttaccg ttaatgaaca gggccaggtt     2280
accgtgaatg gtaaagcaac caaaggtgat gcacatattc tcgagcacca ccaccaccac     2340
cactga                                                               2346
```

<210> SEQ ID NO 17
<211> LENGTH: 22
<212> TYPE: PRT
<213> ORGANISM: Artificial Sequence
<220> FEATURE:

<223> OTHER INFORMATION: Linker N

<400> SEQUENCE: 17

Ser Ala Ser Ala Ser Ala Ser Ala Gly Ala Ser Ala Ala Ala Ser Ala
1               5                   10                  15

Gly Ala Gly Ala Gly Ala
            20

<210> SEQ ID NO 18
<211> LENGTH: 100
<212> TYPE: PRT
<213> ORGANISM: Homo sapiens
<220> FEATURE:
<223> OTHER INFORMATION: Tenth type III module of Fibronectin

<400> SEQUENCE: 18

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Gly Arg
65                  70                  75                  80

Gly Asp Ser Pro Ala Ser Ser Lys Pro Ile Ser Ile Asn Tyr Arg Thr
                85                  90                  95

Glu Ile Pro Ser
            100

<210> SEQ ID NO 19
<211> LENGTH: 744
<212> TYPE: PRT
<213> ORGANISM: Artificial Sequence
<220> FEATURE:
<223> OTHER INFORMATION: FB10-L_N-ADF3-L_N-FB10-H6 fusion protein

<400> SEQUENCE: 19

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Val Thr Val Arg
            20                  25                  30

Tyr Tyr Arg Ile Thr Tyr Gly Glu Thr Gly Gly Asn Ser Pro Val Gln
        35                  40                  45

Glu Phe Thr Val Pro Gly Ser Lys Ser Thr Ala Thr Ile Ser Gly Leu
    50                  55                  60

Lys Pro Gly Val Asp Tyr Thr Ile Thr Val Tyr Ala Val Thr Gly Arg
65                  70                  75                  80

Gly Asp Ser Pro Ala Ser Ser Lys Pro Ile Ser Ile Asn Tyr Arg Thr
                85                  90                  95

Glu Ile Pro Ser Ala Ser Ala Ser Ala Ser Ala Gly Ala Ser Ala Ala
            100                 105                 110

Ala Ser Ala Gly Ala Gly Ala Gly Ala Gly Pro Gly Gln Gln Gly Pro
        115                 120                 125

Gly Gln Gln Gly Pro Gly Gln Gln Gly Pro Tyr Gly Pro Gly Ala Ser
    130                 135                 140

Ala Ala Ala Ala Ala Ala Gly Gly Tyr Gly Pro Gly Ser Gly Gln Gln

-continued

```
            145                 150                 155                 160
Gly Pro Ser Gln Gln Gly Pro Gln Gln Gly Pro Gly Gln Gly
                    165                 170                 175
Pro Tyr Gly Pro Gly Ala Ser Ala Ala Ala Ala Ala Gly Gly Tyr
                180                 185                 190
Gly Pro Gly Ser Gly Gln Gln Gly Pro Gly Gln Gly Pro Tyr Gly
            195                 200                 205
Pro Gly Ser Ser Ala Ala Ala Ala Ala Gly Gly Asn Gly Pro Gly
        210                 215                 220
Ser Gly Gln Gln Gly Ala Gly Gln Gln Gly Pro Gly Gln Gln Gly Pro
225                 230                 235                 240
Gly Gly Ser Ala Ala Ala Ala Ala Gly Gly Tyr Gly Pro Gly Ser
                245                 250                 255
Gly Gln Gln Gly Pro Gly Gln Gln Gly Pro Gly Gln Gly Pro Tyr
                260                 265                 270
Gly Pro Gly Ala Ser Ala Ala Ala Ala Ala Gly Gly Tyr Gly Pro
                275                 280                 285
Gly Ser Gly Gln Gly Pro Gly Gln Gln Gly Pro Gly Gln Gly Pro
            290                 295                 300
Tyr Gly Pro Gly Ala Ser Ala Ala Ala Ala Ala Gly Gly Tyr Gly
305                 310                 315                 320
Pro Gly Ser Gly Gln Gln Gly Pro Gly Gln Gln Gly Pro Gly Gln Gln
                325                 330                 335
Gly Pro Gly Gly Gln Gly Pro Tyr Gly Pro Gly Ala Ser Ala Ala Ala
            340                 345                 350
Ala Ala Ala Gly Gly Tyr Gly Pro Gly Tyr Gly Gln Gln Gly Pro Gly
            355                 360                 365
Gln Gln Gly Pro Gly Gln Gly Pro Tyr Gly Pro Gly Ala Ser Ala
            370                 375                 380
Ala Ser Ala Ala Ser Gly Gly Tyr Gly Pro Gly Ser Gly Gln Gln Gly
385                 390                 395                 400
Pro Gly Gln Gln Gly Pro Gly Gln Gly Pro Tyr Gly Pro Gly Ala
                405                 410                 415
Ser Ala Ala Ala Ala Ala Gly Gly Tyr Gly Pro Gly Ser Gly Gln
            420                 425                 430
Gln Gly Pro Gly Gln Gln Gly Pro Gly Gln Gln Gly Pro Gly Gln Gln
            435                 440                 445
Gly Pro Gly Gly Gln Gly Pro Tyr Gly Pro Gly Ala Ser Ala Ala Ala
        450                 455                 460
Ala Ala Ala Gly Gly Tyr Gly Pro Gly Ser Gly Gln Gln Gly Pro Gly
465                 470                 475                 480
Gln Gln Gly Pro Gly Gln Gln Gly Pro Gly Gln Gln Gly Pro Gly Gln
                485                 490                 495
Gln Gly Pro Gly Gln Gln Gly Pro Gly Gln Gln Gly Pro Gly Gln Gln
                500                 505                 510
Gly Pro Gly Gln Gln Gly Pro Gly Gln Gly Ala Tyr Gly Pro Gly
            515                 520                 525
Ala Ser Ala Ala Ala Gly Ala Ala Gly Tyr Gly Pro Gly Ser Gly
            530                 535                 540
Gln Gln Gly Pro Gly Gln Gln Gly Pro Gly Gln Gln Gly Pro Gly Gln
545                 550                 555                 560
Gln Gly Pro Gly Gln Gln Gly Pro Gly Gln Gln Gly Pro Gly Gln Gln
                565                 570                 575
```

```
Gly Pro Gly Gln Gln Gly Pro Tyr Gly Pro Gly Ala Ser Ala Ala Ala
            580                 585                 590

Ala Ala Ala Gly Gly Tyr Gly Pro Gly Ser Gly Gln Gln Gly Pro Gly
            595                 600                 605

Gln Gln Gly Pro Gly Gln Gln Gly Pro Gly Gly Gln Ala Ser Ala Ser
            610                 615                 620

Ala Ser Ala Ala Ala Ser Ala Ala Ser Thr Val Ala Asn Ser Ser Ser
625                 630                 635                 640

Val Ser Asp Val Pro Arg Asp Leu Glu Val Val Ala Ala Thr Pro Thr
                645                 650                 655

Ser Leu Leu Ile Ser Trp Asp Ala Pro Ala Val Thr Val Arg Tyr Tyr
            660                 665                 670

Arg Ile Thr Tyr Gly Glu Thr Gly Gly Asn Ser Pro Val Gln Glu Phe
            675                 680                 685

Thr Val Pro Gly Ser Lys Ser Thr Ala Thr Ile Ser Gly Leu Lys Pro
            690                 695                 700

Gly Val Asp Tyr Thr Ile Thr Val Tyr Ala Val Thr Gly Arg Gly Asp
705                 710                 715                 720

Ser Pro Ala Ser Ser Lys Pro Ile Ser Ile Asn Tyr Arg Thr Glu Ile
                725                 730                 735

Leu Glu His His His His His His
            740

<210> SEQ ID NO 20
<211> LENGTH: 175
<212> TYPE: PRT
<213> ORGANISM: Homo sapiens
<220> FEATURE:
<223> OTHER INFORMATION: gamma-crystallin D

<400> SEQUENCE: 20

Met Gly Lys Ile Thr Leu Tyr Glu Asp Arg Gly Phe Gln Gly Arg His
1               5                   10                  15

Tyr Glu Cys Ser Ser Asp His Pro Asn Leu Gln Pro Tyr Leu Ser Arg
                20                  25                  30

Cys Asn Ser Ala Arg Val Asp Ser Gly Cys Trp Met Leu Tyr Glu Gln
            35                  40                  45

Pro Asn Tyr Ser Gly Leu Gln Tyr Phe Leu Arg Arg Gly Asp Tyr Ala
        50                  55                  60

Asp His Gln Gln Trp Met Gly Leu Ser Asp Ser Val Arg Ser Cys Arg
65                  70                  75                  80

Leu Ile Pro His Ser Gly Ser His Arg Ile Arg Leu Tyr Glu Arg Glu
                85                  90                  95

Asp Tyr Arg Gly Gln Met Ile Glu Phe Thr Glu Asp Cys Ser Cys Leu
            100                 105                 110

Gln Asp Arg Phe Arg Phe Asn Glu Ile His Ser Leu Asn Val Leu Glu
        115                 120                 125

Gly Ser Trp Val Leu Tyr Glu Leu Ser Asn Tyr Arg Gly Arg Gln Tyr
130                 135                 140

Leu Leu Met Pro Gly Asp Tyr Arg Arg Tyr Gln Asp Trp Gly Ala Thr
145                 150                 155                 160

Asn Ala Arg Val Gly Ser Leu Arg Arg Val Ile Asp Phe Ser Pro
                165                 170                 175

<210> SEQ ID NO 21
```

```
<211> LENGTH: 897
<212> TYPE: PRT
<213> ORGANISM: Artificial Sequence
<220> FEATURE:
<223> OTHER INFORMATION: CRYS-L_N-ADF3-L_c-CRYS-H6 fusion protein

<400> SEQUENCE: 21
```

| | | | | | | | | | | | | | | |
|---|---|---|---|---|---|---|---|---|---|---|---|---|---|---|
| Met | Gly | Lys | Ile | Thr | Leu | Tyr | Glu | Asp | Arg | Gly | Phe | Gln | Gly | Arg | His |
| 1 | | | | 5 | | | | | 10 | | | | | 15 | |
| Tyr | Glu | Cys | Ser | Ser | Asp | His | Pro | Asn | Leu | Gln | Pro | Tyr | Leu | Ser | Arg |
| | | | 20 | | | | | 25 | | | | | 30 | | |
| Cys | Asn | Ser | Ala | Arg | Val | Asp | Ser | Gly | Cys | Trp | Met | Leu | Tyr | Glu | Gln |
| | | 35 | | | | | 40 | | | | | 45 | | | |
| Pro | Asn | Tyr | Ser | Gly | Leu | Gln | Tyr | Phe | Leu | Arg | Arg | Gly | Asp | Tyr | Ala |
| | 50 | | | | | 55 | | | | | 60 | | | | |
| Asp | His | Gln | Gln | Trp | Met | Gly | Leu | Ser | Asp | Ser | Val | Arg | Ser | Cys | Arg |
| 65 | | | | | 70 | | | | | 75 | | | | | 80 |
| Leu | Ile | Pro | His | Ser | Gly | Ser | His | Arg | Ile | Arg | Leu | Tyr | Glu | Arg | Glu |
| | | | | 85 | | | | | 90 | | | | | 95 | |
| Asp | Tyr | Arg | Gly | Gln | Met | Ile | Glu | Phe | Thr | Glu | Asp | Cys | Ser | Cys | Leu |
| | | | 100 | | | | | 105 | | | | | 110 | | |
| Gln | Asp | Arg | Phe | Arg | Phe | Asn | Glu | Ile | His | Ser | Leu | Asn | Val | Leu | Glu |
| | | 115 | | | | | 120 | | | | | 125 | | | |
| Gly | Ser | Trp | Val | Leu | Tyr | Glu | Leu | Ser | Asn | Tyr | Arg | Gly | Arg | Gln | Tyr |
| | 130 | | | | | 135 | | | | | 140 | | | | |
| Leu | Leu | Met | Pro | Gly | Asp | Tyr | Arg | Arg | Tyr | Gln | Asp | Trp | Gly | Ala | Thr |
| 145 | | | | | 150 | | | | | 155 | | | | | 160 |
| Asn | Ala | Arg | Val | Gly | Ser | Leu | Arg | Arg | Val | Ile | Asp | Phe | Ser | Pro | Ser |
| | | | | 165 | | | | | 170 | | | | | 175 | |
| Ala | Ser | Ala | Ser | Ala | Ser | Ala | Gly | Ala | Ser | Ala | Ala | Ser | Ala | Gly |
| | | | 180 | | | | | 185 | | | | | 190 | | |
| Ala | Gly | Ala | Gly | Ala | Gly | Pro | Gly | Gln | Gln | Gly | Pro | Gly | Gln | Gln | Gly |
| | | 195 | | | | | 200 | | | | | 205 | | | |
| Pro | Gly | Gln | Gln | Gly | Pro | Tyr | Gly | Pro | Gly | Ala | Ser | Ala | Ala | Ala |
| | 210 | | | | | 215 | | | | | 220 | | | | |
| Ala | Ala | Gly | Gly | Tyr | Gly | Pro | Gly | Ser | Gly | Gln | Gln | Gly | Pro | Ser | Gln |
| 225 | | | | | 230 | | | | | 235 | | | | | 240 |
| Gln | Gly | Pro | Gly | Gln | Gly | Pro | Gly | Gln | Gly | Pro | Tyr | Gly | Pro |
| | | | | 245 | | | | | 250 | | | | | 255 | |
| Gly | Ala | Ser | Ala | Ala | Ala | Ala | Ala | Gly | Gly | Tyr | Gly | Pro | Gly | Ser |
| | | | 260 | | | | | 265 | | | | | 270 | | |
| Gly | Gln | Gln | Gly | Pro | Gly | Gln | Gly | Pro | Tyr | Gly | Pro | Gly | Ser | Ser |
| | | 275 | | | | | 280 | | | | | 285 | | | |
| Ala | Ala | Ala | Ala | Ala | Gly | Asn | Gly | Pro | Gly | Ser | Gly | Gln | Gln |
| | 290 | | | | | 295 | | | | | 300 | | | | |
| Gly | Ala | Gly | Gln | Gln | Gly | Pro | Gly | Gln | Gln | Gly | Pro | Gly | Gly | Ser | Ala |
| 305 | | | | | 310 | | | | | 315 | | | | | 320 |
| Ala | Ala | Ala | Ala | Ala | Gly | Gly | Tyr | Gly | Pro | Gly | Ser | Gly | Gln | Gln | Gly |
| | | | | 325 | | | | | 330 | | | | | 335 | |
| Pro | Gly | Gln | Gln | Gly | Pro | Gly | Gln | Gln | Gly | Pro | Tyr | Gly | Pro | Gly | Ala |
| | | | 340 | | | | | 345 | | | | | 350 | | |
| Ser | Ala | Ala | Ala | Ala | Ala | Gly | Gly | Tyr | Gly | Pro | Gly | Ser | Gly | Gln |
| | | 355 | | | | | 360 | | | | | 365 | | | |
| Gly | Pro | Gly | Gln | Gln | Gly | Pro | Gly | Gln | Gly | Pro | Tyr | Gly | Pro | Gly |
| | 370 | | | | | 375 | | | | | 380 | | | | |

```
Ala Ser Ala Ala Ala Ala Ala Gly Gly Tyr Gly Pro Gly Ser Gly
385                 390                 395                 400

Gln Gln Gly Pro Gly Gln Gln Gly Pro Gly Gln Gln Gly Pro Gly Gly
            405                 410                 415

Gln Gly Pro Tyr Gly Pro Gly Ala Ser Ala Ala Ala Ala Ala Gly
            420                 425                 430

Gly Tyr Gly Pro Gly Tyr Gly Gln Gln Gly Pro Gly Gln Gln Gly Pro
            435                 440                 445

Gly Gly Gln Gly Pro Tyr Gly Pro Gly Ala Ser Ala Ala Ser Ala Ala
        450                 455                 460

Ser Gly Gly Tyr Gly Pro Gly Ser Gly Gln Gln Gly Pro Gly Gln Gln
465                 470                 475                 480

Gly Pro Gly Gly Gln Gly Pro Tyr Gly Pro Gly Ala Ser Ala Ala Ala
            485                 490                 495

Ala Ala Ala Gly Gly Tyr Gly Pro Gly Ser Gly Gln Gln Gly Pro Gly
            500                 505                 510

Gln Gln Gly Pro Gly Gln Gln Gly Pro Gly Gln Gln Gly Pro Gly Gly
            515                 520                 525

Gln Gly Pro Tyr Gly Pro Gly Ala Ser Ala Ala Ala Ala Ala Gly
            530                 535                 540

Gly Tyr Gly Pro Gly Ser Gly Gln Gln Gly Pro Gly Gln Gln Gly Pro
545                 550                 555                 560

Gly Gln Gln Gly Pro Gly Gln Gln Gly Pro Gly Gln Gln Gly Pro Gly
            565                 570                 575

Gln Gln Gly Pro Gly Gln Gln Gly Pro Gly Gln Gln Gly Pro Gly Gln
            580                 585                 590

Gln Gly Pro Gly Gly Gln Gly Ala Tyr Gly Pro Gly Ala Ser Ala Ala
            595                 600                 605

Ala Gly Ala Ala Gly Gly Tyr Gly Pro Gly Ser Gly Gln Gln Gly Pro
        610                 615                 620

Gly Gln Gln Gly Pro Gly Gln Gln Gly Pro Gly Gln Gln Gly Pro Gly
625                 630                 635                 640

Gln Gln Gly Pro Gly Gln Gln Gly Pro Gly Gln Gln Gly Pro Gly Gln
            645                 650                 655

Gln Gly Pro Tyr Gly Pro Gly Ala Ser Ala Ala Ala Ala Ala Gly
            660                 665                 670

Gly Tyr Gly Pro Gly Ser Gly Gln Gln Gly Pro Gly Gln Gln Gly Pro
            675                 680                 685

Gly Gln Gln Gly Pro Gly Gly Gln Ala Ser Ala Ser Ala Ser Ala Ala
            690                 695                 700

Ala Ser Ala Ala Ser Thr Val Ala Asn Ser Ser Ser Gly Lys Ile Thr
705                 710                 715                 720

Leu Tyr Glu Asp Arg Gly Phe Gln Gly Arg His Tyr Glu Cys Ser Ser
            725                 730                 735

Asp His Pro Asn Leu Gln Pro Tyr Leu Ser Arg Cys Asn Ser Ala Arg
            740                 745                 750

Val Asp Ser Gly Cys Trp Met Leu Tyr Glu Gln Pro Asn Tyr Ser Gly
            755                 760                 765

Leu Gln Tyr Phe Leu Arg Arg Gly Asp Tyr Ala Asp His Gln Gln Trp
            770                 775                 780

Met Gly Leu Ser Asp Ser Val Arg Ser Cys Arg Leu Ile Pro His Ser
785                 790                 795                 800
```

```
Gly Ser His Arg Ile Arg Leu Tyr Glu Arg Glu Asp Tyr Arg Gly Gln
                805                 810                 815

Met Ile Glu Phe Thr Glu Asp Cys Ser Cys Leu Gln Ser Arg Phe Arg
            820                 825                 830

Phe Asn Glu Ile His Ser Leu Asn Val Leu Glu Gly Ser Trp Val Leu
        835                 840                 845

Tyr Glu Leu Ser Asn Tyr Arg Gly Arg Gln Tyr Leu Leu Met Pro Gly
    850                 855                 860

Asp Tyr Arg Arg Tyr Gln Asp Trp Gly Ala Thr Asn Ala Arg Val Gly
865                 870                 875                 880

Ser Leu Arg Arg Val Ile Asp Phe Ser Leu Glu His His His His
                885                 890                 895

His
```

<210> SEQ ID NO 22
<211> LENGTH: 2228
<212> TYPE: DNA
<213> ORGANISM: Artificial Sequence
<220> FEATURE:
<223> OTHER INFORMATION: Nucleic acid sequence encoding fusion protein
      FB10-L_N-ADF3-L_N-FB10-H6

<400> SEQUENCE: 22

```
tgttagtgat gttccgcgtg atctggaagt tgttgcagca accccgacca gcctgctgat    60
tagctgggat gcaccggcag ttaccgttcg ttattatcgt attacctatg gtgaaaccgg   120
tggtaatagt ccggttcaag aatttaccgt tccgggtagc aaaagcaccg caaccattag   180
cggtctgaaa ccgggtgttg attacaccat taccgtttat gccgttaccg tcgtggtga   240
ttcaccggca agcagcaaac cgattagcat taactatcgt accgaaattc gagcgctag   300
cgcaagcgca agtgccggtg caagcgcagc agcatcagcc ggtgctggtg caggcgccgg   360
cccgggtcag caaggcccag acagcaagg cccgggtcag cagggaccgt acggccctgg   420
tgcctcggcc gcagcagctg cagcaggagg atatggacct ggatctggtc agcagggccc   480
gtcgcagcag ggcccgggtc aacaaggccc aggcggccag ggcccgtatg accgggggc   540
gagtgccgct gccgctgccg ctggcggtta tgggcctggg tcaggtcagc aaggtcctgg   600
gggtcaggga ccatatgggc ctgggagttc ggccgcagcc gctgcggcgg cggtaatgg   660
gcctggctcc gggcaacaag cgctggtca acaaggacct gggcagcagg ggccgggcgg   720
tagcgctgcg gcagcagctg caggtgggta cggtccagga tcgggacaac aaggaccagg   780
tcaacagggg cctggcgggc aaggacctta tgggccggga gcctccgcgg cggcggctgc   840
agctggtggt tacggaccgg ggtcaggcca aggaccgggc agcagggac cgggggggca   900
gggtccatac ggcccagggg cttcagcagc tgcagcagcg gcgggcggct atggtcctgg   960
ttcgggccag caaggccag ggcaacaagg tccagggcaa caagggcctg cgggcaagg   1020
accttacggc ccaggagcgt cagcggcgg tgcggctgcc gggggctacg gcccgggcta   1080
tggtcagcag gggccgggtc agcagggacc gggtggtcag gggccatatg gtccaggggc   1140
ctctgccgca agcgcggcga gtggggcta tgggccgggc tcgggacagc agggccctgg   1200
ccagcagggg ccaggggggcc aaggaccgta tggaccaggc gcatcggcgg cagccgccgc   1260
ggcgggagga tatggtcctg ggagcggtca gcagggaccg ggccagcaag gacctggtca   1320
gcaagggcca ggtcaacaag ggcccggtgg gcaagggcca tacggccag agcctcagc   1380
agcggctgcc gcggctggtg ggtacggtcc gggttcgggc cagcaaggac ctggacaaca   1440
```

| | |
|---|---:|
| gggtccaggt cagcaaggcc caggccaaca gggtccgggg cagcaagggc caggtcagca | 1500 |
| aggtcctggt caacaaggtc cagggcagca gggaccgggc cagcaagggc caggcggtca | 1560 |
| aggtgcgtat ggaccggggg catctgccgc tgcaggggcc gccggtggtt atggcccggg | 1620 |
| ctccgggcag caagggcctg gcaacaggg gcctggccaa caaggcccag acagcaagg | 1680 |
| tccaggccaa caggggcctg gcaacaagg gcctggccag caagggcctg gccaacaagg | 1740 |
| tccgtatggt cctggcgcaa gcgcggcagc ggcggcagcc ggtggatacg cccaggaag | 1800 |
| cgggcaacaa ggtcctgggc agcaggggcc tggtcaacaa ggaccgggcg gtcaggccag | 1860 |
| cgcaagcgca agtgcagcag caagcgcagc cagcaccgtt gcgaattctt ctagcgttag | 1920 |
| tgatgttccg cgtgatctgg aagttgttgc agcaaccccg accagcctgc tgattagctg | 1980 |
| ggatgcaccg gcagttaccg ttcgttatta tcgtattacc tatggtgaaa ccggtggtaa | 2040 |
| tagtccggtt caagaattta ccgttccggg tagcaaaagc accgcaacca ttagcggtct | 2100 |
| gaaaccgggt gttgattaca ccattaccgt ttatgccgtt accggtcgtg gtgattcacc | 2160 |
| ggcaagcagc aaaccgatta gcattaacta tcgtaccgaa attctcgagc accaccacca | 2220 |
| ccaccact | 2228 |

<210> SEQ ID NO 23
<211> LENGTH: 2689
<212> TYPE: DNA
<213> ORGANISM: Artificial Sequence
<220> FEATURE:
<223> OTHER INFORMATION: Nucleic acid sequence encoding fusion
      proteinCRYS-L_N-ADF3-L_c-CRYS-H6

<400> SEQUENCE: 23

| | |
|---|---:|
| tgggtaaaat taccctgtat gaagatcgtg ttttcaggg tcgtcattat gaatgtagca | 60 |
| gcgatcatcc gaatctgcag ccgtatctga gccgttgtaa tagcgcacgt gttgatagcg | 120 |
| gttgttggat gctgtatgaa cagccgaatt atagtggtct gcagtatttt ctgcgtcgcg | 180 |
| gtgattatgc agatcatcag cagtggatgg gtctgagcga tagcgttcgt agctgtcgtc | 240 |
| tgattccgca tagcggtagc catcgtattc gtctgtatga gcgtgaagat tatcgtggtc | 300 |
| agatgattga atttacggaa gattgtagct gtctgcagga tcgtttttcgc tttaatgaaa | 360 |
| ttcatagcct gaatgtgctg gaaggtagct gggttctgta cgaactgagc aattatcgcg | 420 |
| gtcgtcagta tctgctgatg cctggtgatt atcgtcgtta tcaggattgg ggtgcaacca | 480 |
| atgcgcgtgt tggtagcctg cgtcgtgtta ttgattttag cccgagcgct agcgcaagcg | 540 |
| catcagcccg tgcaagtgct gcagcaagtc ccggtgctgg tgcgggtgca ggtcctggtc | 600 |
| agcagggtcc gggtcaacaa ggacctggac agcaaggacc gtatggtcca ggtgcatcag | 660 |
| ctgcagccgc agcagcgggt ggttatggtc cgggaagcgg tcagcaaggc ccttcacaac | 720 |
| agggaccagg ccaacagggt cctggcggtc aaggtcctta tggacctggt gcttctgctg | 780 |
| cggcagcggc tgccggtggc tatgccctg tagtggcca gcaagggcct ggtggccagg | 840 |
| gtccatatgg cccaggttct agtgccgcag ctgctgctgc aggcggtaat ggaccgggtt | 900 |
| caggacaaca aggtgcaggg cagcaaggtc ccggacaaca gggtccaggt ggtagtgcag | 960 |
| cagcggcagc agctggcgga tatggaccag gtagtggca caaggccca ggtcaacaag | 1020 |
| gccaggggg tcaaggccca tacggtccgg gtgcttccgc agccgcagct gcagcaggcg | 1080 |
| gttacggtcc tggtagtggt caaggtccag gccagcaagg accaggtgga caagggcctt | 1140 |
| acggaccagg cgcatctgcg gcagcagcag ccgcagggg atatggtcct ggttcagggc | 1200 |

```
agcagggacc aggtcagcaa ggtccaggtc agcagggacc tgggggtcag ggaccttacg    1260
gtcctggcgc aagtgcagct gcagcggcag cgggtggcta cggaccgggt tatggccagc    1320
agggaccggg acagcaggga cccggtggac agggtccgta tggaccgggt gcaagtgcag    1380
catcagcagc aagtggtggt tacgacctg gctcaggaca gcaaggccct ggccaacaag     1440
gccctggcgg acagggaccc tatgggccag gtgccagcgc tgcagcagcc gcagccggtg    1500
gatacggtcc aggctctggt caacaaggtc ctgggcaaca aggtcctggc cagcagggtc    1560
caggacagca agggcctggc ggtcaaggac cgtacgacc gggtgccagc gcagcggctg     1620
cagcggcagc cggttatggt ccaggatcag gccagcaagg tccgggtcag caaggcccag    1680
ggcagcaagg accgggtcaa cagggaccgg gtcagcaggg tcctgggcaa cagggtccgg    1740
gacaacaggg accaggtcaa caaggaccgg gtcaacaagg tccaggtggt cagggtgcat    1800
atggtcctgg cgcttcagca gcagcagggg ctgcagggg ttatggccca ggtagcggtc     1860
agcagggacc cggacaacaa ggccctggac aacagggtcc cggtcagcaa gggccaggcc    1920
aacaaggtcc aggacaacaa ggaccagggc agcagggtcc aggccaacaa ggcccttatg    1980
gtccgggtgc cagtgctgcg gcagcggcag ctgggggtta tggtccaggc tctggacagc    2040
agggacctgg ccagcaagga cctgggcagc aagggccagg cggtcaggca agtgcatcag    2100
caagcgcagc agcgagtgca gcaagcaccg ttgcgaattc tagctccggt aaaattaccc    2160
tgtatgaaga tcgtggtttt cagggtcgtc attatgaatg tagcagcgat catccgaatc    2220
tgcagccgta tctgagccgt tgtaatagcg cacgtgttga tagcggttgt tggatgctgt    2280
atgaacagcc gaattatagt ggtctgcagt attttctgcg tcgcggtgat tatgcagatc    2340
atcagcagtg gatgggtctg agcgatagcg ttcgtagctg tcgtctgatt ccgcatagcg    2400
gtagccatcg tattcgtctg tatgagcgtg aagattatcg tggtcagatg attgaattta    2460
cggaagattg tagctgtctg caggatcgtt ttcgctttaa tgaaattcat agcctgaatg    2520
tgctggaagg tagctgggtt ctgtacgaac tgagcaatta tcgcggtcgt cagtatctgc    2580
tgatgcctgg tgattatcgt cgttatcagg attggggtgc aaccaatgcg cgtgttggta    2640
gcctgcgtcg tgttattgat tttagcctcg agcaccacca ccaccacca               2689
```

METHOD FOR PRODUCING A CONDENSED ADHESIVE PHASE OF SILK FUSION PROTEINS

FIELD OF THE INVENTION

The present invention relates to the production of recombinant spider silk proteins and to the use of the proteins in the field of materials, biotechnology, and medicine. The present invention is particularly related to applications involving preparation of composite materials, textiles, filters, biomedical coatings, wound dressings, drug release materials, cell scaffolds, adhesives, etc.

BACKGROUND OF THE INVENTION

Silk and silk-like proteins are a large group of proteins found in many different organisms where they fulfill a variety of different roles. A very well-known example is the domesticated silk moth *Bombyx mori* that is used on an industrial scale to produce silk fiber. Related silk-proteins are produced by for example by spiders when making webs[1]. Also, other organisms, for example, mussels produce silk-like proteins as part of the nacreous structures in their shells[2]. Because of the structural properties of silk-like proteins in natural materials are very desirable, there is a large industrial interest in making silk-like proteins. One envisions that industrially produced silk-like proteins could replace current synthetic or other natural polymers in specific applications or on a large scale. Although *Bombyx mori* silk is widely used, there are limitations to its use and industrial scale-up. It is desirable to use recombinant organisms or cells that can be grown in bioreactors to produce silk-like proteins, because of scalability and process considerations. It is also desirable to produce silk-like proteins in forms that are not naturally found in order to make new types of silk-like polymer materials[3].

In the literature, the problem of forming fibers by recombinantly produced silk proteins is well documented. The invention relates to the general problem of processing recombinantly produced silk protein into a state from which, for example, fibers can be made and that is in a state that naturally produced silk proteins, such as spider webs, are found. As a first step bacteria or eukaryotic cells are used to produce the silk-like proteins. For this, standard methods of recombinant DNA technology are used[4]. A typical way to proceed is to collect the recombinant protein produced by said organisms in an aqueous solution, which can be the medium in which the organisms have been grown in. Often the silk proteins are then precipitated from the solution. After precipitation the silk protein is collected and often lyophilized[5]. The collected and precipitated protein is then dissolved using some solubilization chemicals such as 1,1,1,3,3,3-hexafluoro-2-propanol (HFIP)[6-10], lithium bromide (LiBr)[11], or guanidinium thiocyanate (GdmSCN)[12]. In the next step, the excess solubilization chemicals are removed by, for example, dialysis or other forms of buffer exchange. The silk protein solution is typically concentrated or desalted, and then extruded into a coagulation bath containing an antisolvent such as methanol or isopropanol[10,12,13]. Sometimes this procedure is performed using microfluidic devices[14,15]. Alternative ways are also described. For example, the silk protein solution can also be processed by electrospinning to produce fibers[16,17].

Sometimes the protein is not purified by precipitation, but instead using chromatographic techniques. In these cases, a polypeptide tag is genetically fused to the silk-proteins. These tags are, for example, sequences of histidine residues (His-tags), thioredoxin (Trx)[18], or a SUMO tag[19]. When removing tags (such as Trx or SUMO) the solubility of the protein decreases and fiber formation can occur. In these cases, fibrils are formed in the solution or at the air-water interface and the fibers can be pulled out of the aqueous solution[6].

The present invention addresses the problem of how silk proteins can be produced and processed for assembly into fibers or other structures such as films or coatings in a way that does not require precipitation of the silk protein nor subsequent solubilizing the protein. The invention does not require the use of fusion tags that must be removed by processing with protease enzymes or other means of cleavage of fusion protein tags[20]. The invention allows production of fibers of recombinant silk proteins without the use of coagulation baths such as isopropanol or methanol. Because the steps of solubilization, fusion protein removal, and the use of coagulation baths are not needed, there is a significant benefit of the invention in making fibers.

Solubilization of precipitated silk proteins requires the use of harsh chemicals, in particular, HFIP, lithium salts, and GdmSCN are either toxic or add substantial cost to the process. Solubilization can also cause physical damage to the silk proteins. The use of proteases to cleave protein domains prior to assembly require protease enzymes that are expensive and add processing steps such as chromatography that limits scalability.

The present invention discloses a way in which recombinant silk proteins can be brought into a condensed phase which then can be used to form fibers, adhesives, coatings, films, or other material structures.

SUMMARY OF THE INVENTION

It is an aim of the present invention to provide a method of producing materials using recombinant silk proteins by facile processing. The present invention reduces the processing steps needed for silk-like protein purification, as only a concentrating step is required for formation of a concentrated silk-like protein solution. The concentrated silk-like solution forms by a phase separation event and does not involve precipitation of the protein nor subsequent dissolving of the protein. The invention also enables omitting other alternative processing methods such as chromatographic separation and possible removal of tag-proteins by cleavage of peptide-bonds. The invention has the advantage that it enables the formation of fibers directly by stretching or elongating the protein concentrate solution in the air or a gaseous environment. Fibers can be pulled directly from the concentrate without the need for extruding silk-like protein in a liquid bath to coagulate the protein. Thus, this processing step can be omitted. Advantages also include the possibility to make single fiber filaments that are very long. In addition, the invention provides the use of concentrated silk-like solution as a water-based adhesive for gluing a variety of materials and surfaces.

Accordingly, in one aspect the present invention provides a method for producing a condensed phase of a silk fusion protein, the method comprising the steps of a) preparing a solution of a silk fusion protein in an aqueous medium, wherein said fusion protein is isolated from a recombinant production host and comprises a silk-like protein sequence and two separate non-silk terminal module sequences flanking said silk-like protein sequence;

b) concentrating said fusion protein in said aqueous medium, until a liquid phase separation occurs;

c) collecting a protein-rich phase of said aqueous medium obtained in step b)

d) repeating steps b) and c) with the protein-rich phase obtained in step c) until a protein concentration of about 20-45% w/v is reached;

e) optionally separating aggregates of the fusion protein from soluble fusion proteins obtained in step d) and removing the aggregates from the solution;

f) concentrating the solution obtained in step d) or e) to the final protein concentration of about 60-80% w/v, wherein the steps a) to f) are performed so that said silk fusion protein is not precipitated and subsequently dissolved to said aqueous medium.

In another aspect, the present invention provides a concentrate of spider silk fusion protein produced by the above method.

In another aspect, the present invention provides a recombinant spider silk fusion protein comprising silk polymer repeats, wherein the repeat sequence consists of repeat A sequence of SEQ ID NO: 1 combined with repeat Q sequence of SEQ ID NO: 2, and two cellulose binding modules (CBM) from *Clostridium thermocellum* consisting of the sequence of SEQ ID NO:7 flanking said silk polymer repeats, each module linked to said repeats with a C-terminal linker of SEQ ID NO:6 or a N-terminal linker of SEQ ID NO:5.

In another aspect, the present invention provides a recombinant spider silk fusion protein comprising spider silk protein repeat sequence *Araneus diadematus* ADF3 of SEQ ID NO:3, or the *Latrodectus hesperus* AcSp1 sequence of SEQ ID NO:4; and two cellulose binding modules (CBM) from *Clostridium thermocellum* consisting of the sequence of SEQ ID NO:7 flanking said silk protein repeats, each module linked to said repeat sequence ADF3 or the *Latrodectus Hesperus* AcSp1 sequence with a C-terminal linker of SEQ ID NO:6 or a N-terminal linker of SEQ ID NO:5.

In another aspect, the present invention provides a recombinant spider silk fusion protein comprising spider silk protein repeat sequence *Araneus diadematus* ADF3 of SEQ ID NO:3, and two SpyCatcher domains engineered from fibronectin-binding protein FbaB of *Streptococcus pyogenes* consisting of the sequence of SEQ ID NO:14 flanking said silk protein repeat sequence, each domain linked to said repeat sequence ADF3 with a C-terminal linker of SEQ ID NO:6 or a N-terminal linker of SEQ ID NO:17.

In another aspect, the present invention provides a recombinant spider silk fusion protein comprising spider silk protein repeat sequence *Araneus diadematus* ADF3 of SEQ ID NO:3, and two tenth type III modules of Fibronectin from *Homo sapiens* consisting of the sequence of SEQ ID NO:18 flanking said silk protein repeat sequence, each domain linked to said repeat sequence ADF3 with a C-terminal linker of SEQ ID NO:6 or a N-terminal linker of SEQ ID NO:17.

In another aspect, the present invention provides a recombinant spider silk fusion protein comprising spider silk protein repeat sequence *Araneus diadematus* ADF3 of SEQ ID NO:3, and two gamma-crystallin D domains from *Homo sapiens* consisting of the sequence of SEQ ID NO:20 flanking said silk protein repeat sequence, each domain linked to said repeat sequence ADF3 with a C-terminal linker of SEQ ID NO:6 or a N-terminal linker of SEQ ID NO:17.

In another aspect, the present invention provides a recombinant nucleic acid expressing the recombinant spider silk fusion protein as defined above.

In another aspect, the present invention provides a host cell expressing the recombinant nucleic acid expressing the recombinant spider silk fusion protein as defined above.

In another aspect, the present invention provides an adhesive comprising a silk fusion protein as an active ingredient, wherein said silk fusion protein comprises a silk-like protein sequence and two separate non-silk terminal module sequences flanking said silk-like protein sequence.

In another aspect, the present invention is directed to the use of a silk fusion protein as an adhesive, wherein said silk fusion protein comprises a silk-like protein sequence and two separate non-silk terminal module sequences flanking said silk-like protein sequence.

In another aspect, the present invention is directed to a method of making a composite comprising the steps of a) providing a first substrate, b) applying an adhesive comprising a silk fusion protein as an active ingredient as disclosed herein to the substrate, and c) subjecting the substrate obtained from step b) in contact with a second substrate or surface to form the composite, wherein adherence of said first substrate to said second substrate or surface is enhanced by said adhesive.

DESCRIPTION OF EMBODIMENTS

The invention involves forming a protein concentrate from a solution of the silk-like proteins after production of the silk-like proteins in the recombinant production host. The concentrate is formed by concentrating a solution of the silk-like proteins without the need for a purification step such as protein precipitation or chromatographic purification. The concentrate is characterized by being a detectable and separate liquid phase, distinct from the aqueous phase from which it was formed.

The present invention thus provides a method for producing a condensed phase of a silk fusion protein, the method comprising the steps of a) preparing a solution of a silk fusion protein in an aqueous medium, wherein said fusion protein is isolated from a recombinant production host and comprises a silk-like protein sequence and two separate non-silk terminal module sequences flanking said silk-like protein sequence;

b) concentrating said fusion protein in said aqueous medium, until a liquid phase separation occurs;

c) collecting a protein-rich phase of said aqueous medium obtained in step b)

d) repeating steps b) and c) with the protein-rich phase obtained in step c) until a protein concentration of about 20-45% w/v is reached;

e) optionally separating aggregates of the fusion protein from soluble fusion proteins obtained in step d) and removing the aggregates from the solution;

f) concentrating the solution obtained in step d) or e) to the final protein concentration of about 60-80% w/v, wherein the steps a) to f) are performed so that said silk fusion protein is not precipitated and subsequently dissolved to said aqueous medium.

Figure 12:
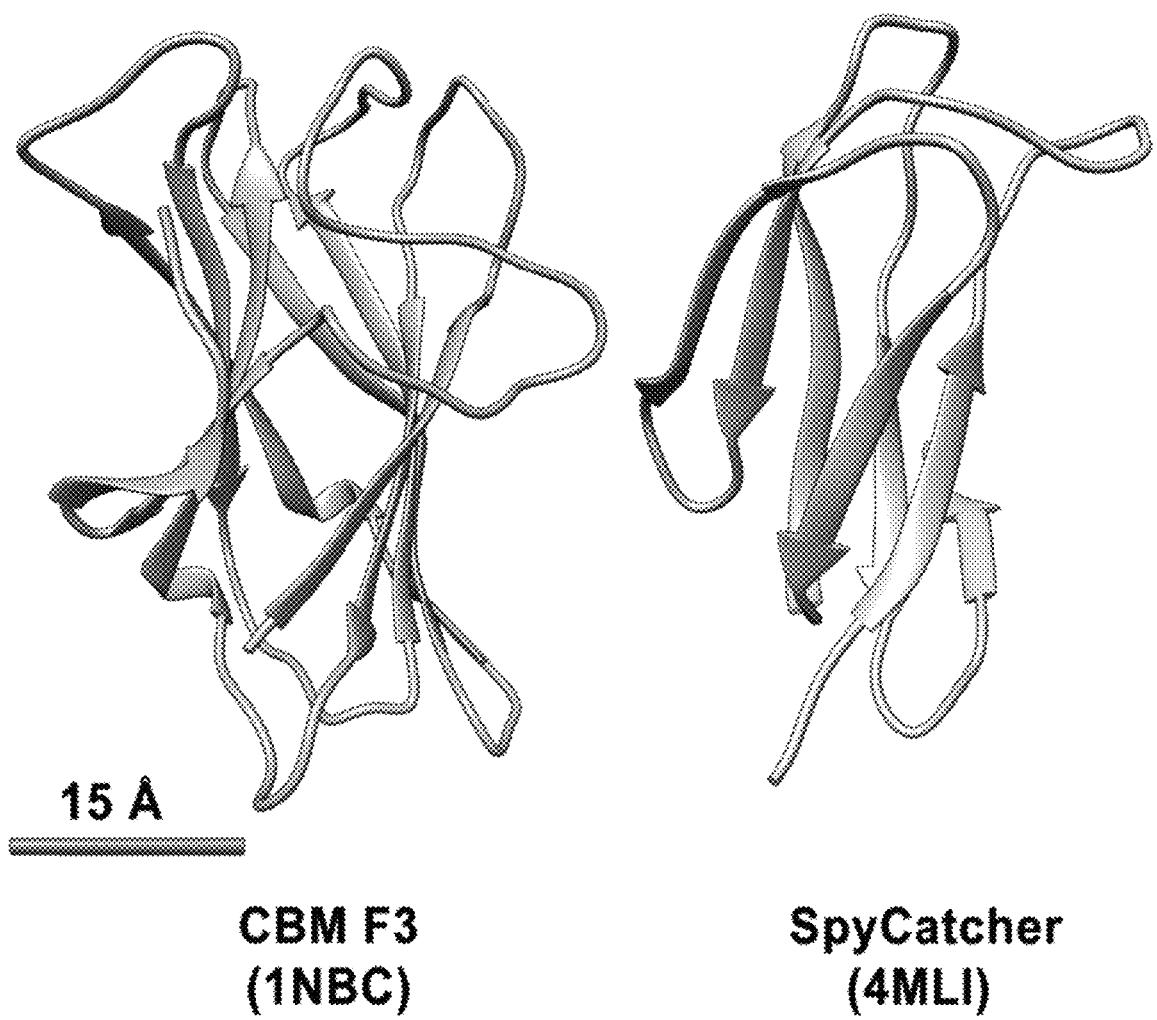
FIG. 12. Three-dimensional structures of the terminal domains. Left panel; Structure of family three cellulose binding module (CBM) from *Clostridium thermocellum* (PDB: 1NBC). Right panel; Structure of SpyCatcher domain from *Streptococcus pyogenes* (PDB: 4MLI).

The expression "non-silk terminal module sequences" refers herein to two protein domains flanking said silk-like protein sequence, said two domains having identical or nearly identical (i.e. at least 80%, 85%, 90%, 91%, 92%, 93%, 94%, 95%, 96%, 97%, 98%, or 99% homology or sequence identity) amino acid sequences. In an alternative embodiment, said non-silk terminal module sequences flanking silk-like protein sequences have similar three-dimensional structures. Said non-silk terminal module sequences are not present in combination with silk proteins sequences in nature. Suitable terminal module sequences for the silk fusion protein of the present invention preferably have the three-dimensional structure as described in FIG. 12. Said three-dimensional structure comprises consecutive β-strands forming a β-sheet, preferably at least four consecutive β-strands. The length of the amino acid sequence for the terminal module is preferably in the range of 90-250 amino acids, more preferably 98-239 amino acids (see Table 1). Preferably, said protein domains are selected from the group of carbohydrate binding modules (CBMs) such as the cellulose binding module from *Clostridium thermocellum* comprising the sequence of SEQ ID NO:7. We also disclose terminal module sequences based on the SpyCatcher domain engineered from fibronectin-binding protein FbaB of *Streptococcus pyogenes* comprising the sequence of SEQ ID NO:14, gamma-crystallin D from *Homo sapiens* comprising the sequence of SEQ ID NO:20, and tenth type III module of Fibronectin from *Homo sapiens* comprising the sequence of SEQ ID NO:18. For other preferred embodiments, suitable terminal module peptides for the silk fusion protein are listed in Table 1. In a preferred embodiment, a non-silk terminal module sequence can be paired with another non-silk terminal module sequence having a corresponding three-dimensional structure. For instance, when one of the flanking terminal module sequences in a silk fusion protein is a CBM, the other can be a SpyCatcher domain.

The term "aqueous medium" refers herein to a liquid medium which preferably can be distilled water or a buffer consisting of water and a mixture of a weak acid and its conjugate base.

The term "a silk-like protein sequence" refers herein to amino acid sequences comprising repetitive sequences capable of forming silk fibrillar structures or silk fibers. Preferably, silk-like protein sequence is a spider silk protein sequence or a variant thereof from a spider of order Araneae.

The term "variant" as used herein means amino acid or nucleic acid sequence having high homology to a parent sequence. Preferably, the variant has 80%, 85%, 90%, 91%, 92%, 93%, 94%, 95%, 96%, 97%, 98%, or 99% homology (i.e. sequence identity) to the parent sequence. Two examples of algorithms that are suitable for determining percent sequence identity and sequence similarity are the BLASTp and BLASTn 2.0 algorithms, which are described in Altschul et al. (1997) Nucleic Acids Res 25(17):3389-3402.

Figure 4:
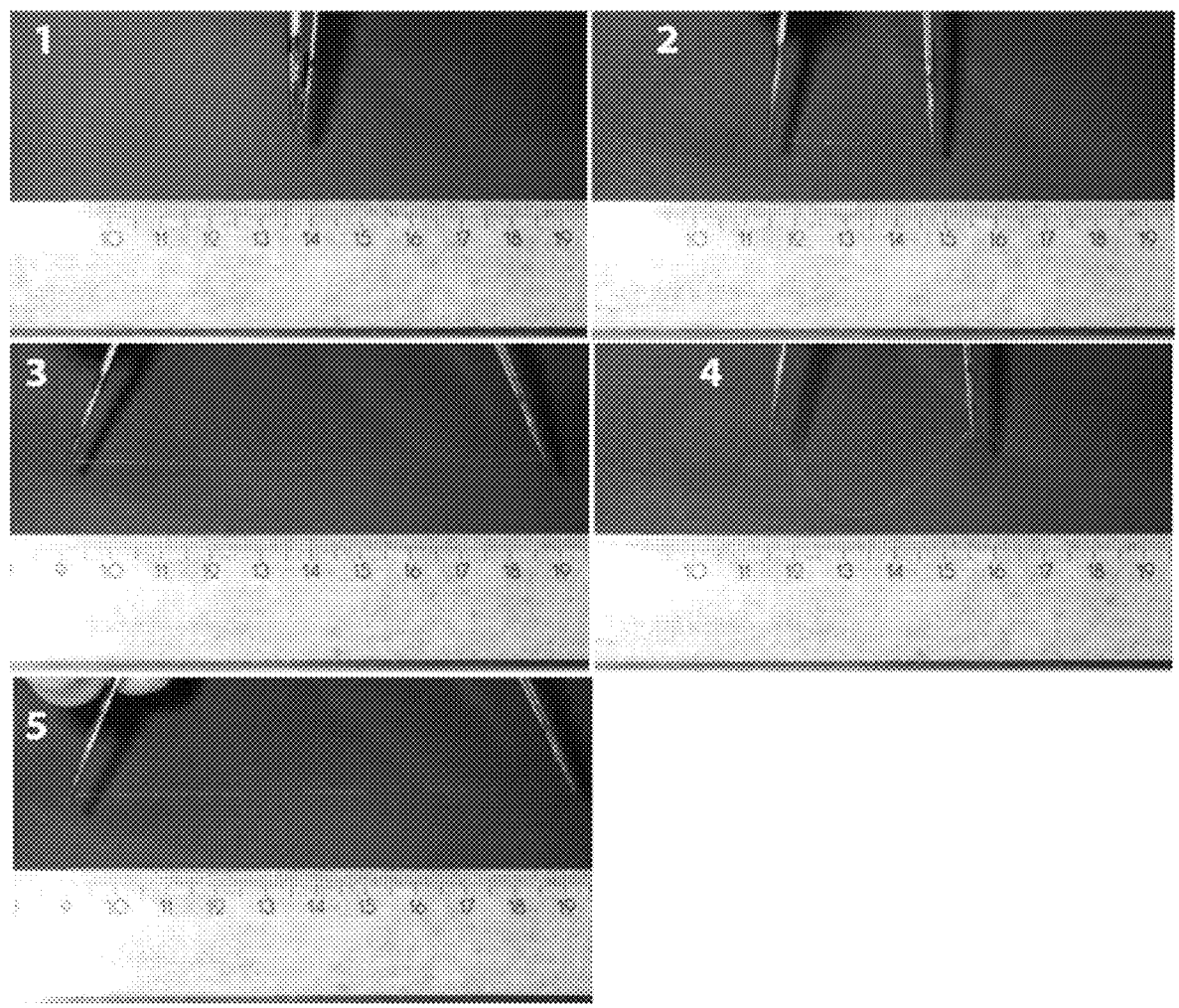
FIG. 4. Pulling of fibers from the phase separated dense protein condensate droplet.
Figure 5:
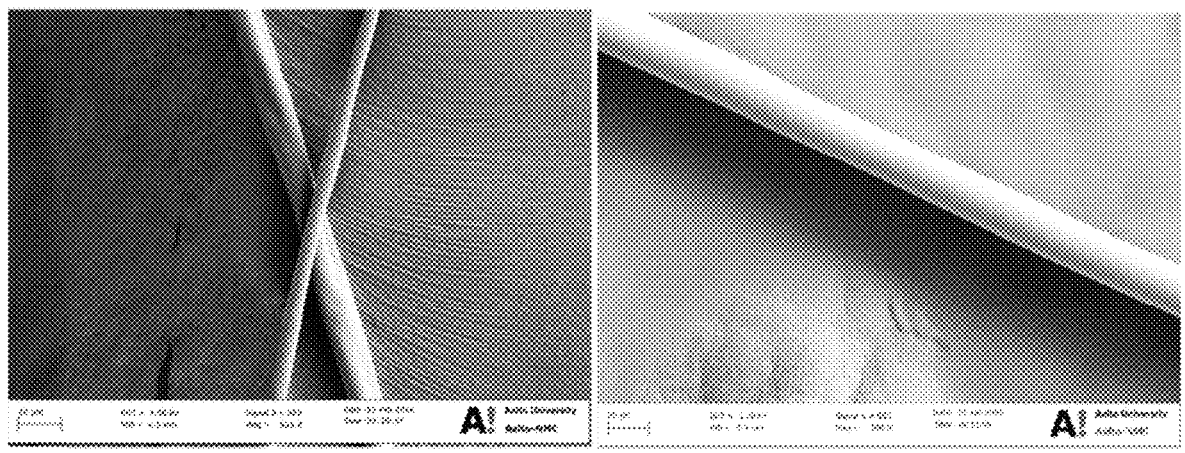
FIG. 5. Scanning electron micrograph of pulled and dried filament from the phase separated dense protein droplet.
Figure 6:
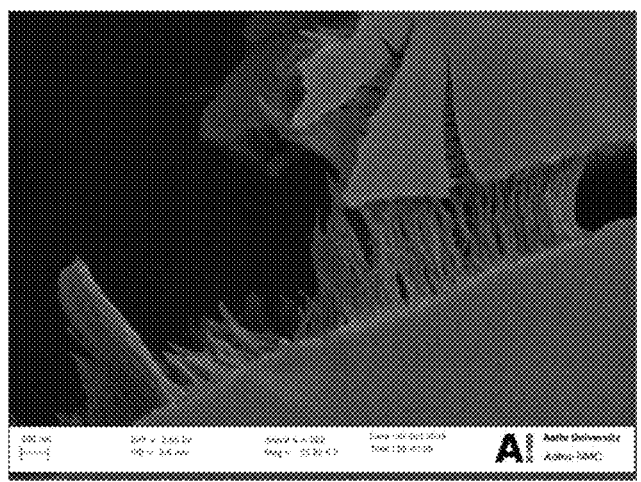
FIG. 6. Silk-like protein concentrate forms fibrous assemblies when deformed by pulling forces.

Preferably, the above method comprises a further step of:

g) preparing silk fusion protein filaments from the concentrate obtained from step f). More preferably, the filaments are prepared in step g) by pulling the filaments from the concentrate by shear force. An example is shown in FIG. 4.

Figures 7A, 7B, 7C, 7D, 7E, 7F:
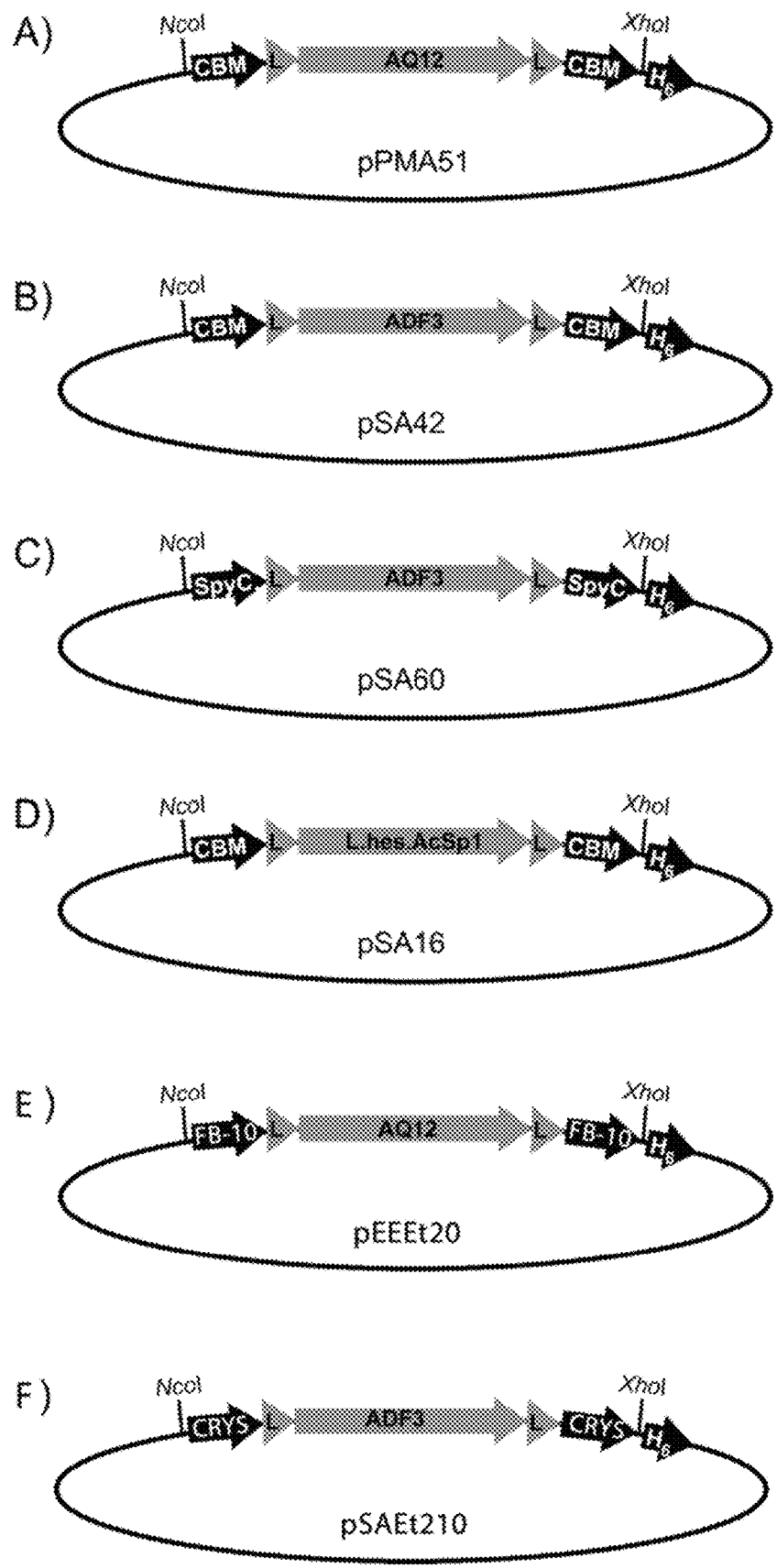
FIG. 7. Schematic drawings of plasmids (A) pPMA51, (B) pSA42, (C) pSA60, (D) pSA16 (E) pEEEt20 and (F) pSAEt210 containing silk like sequences.
Figure 8:
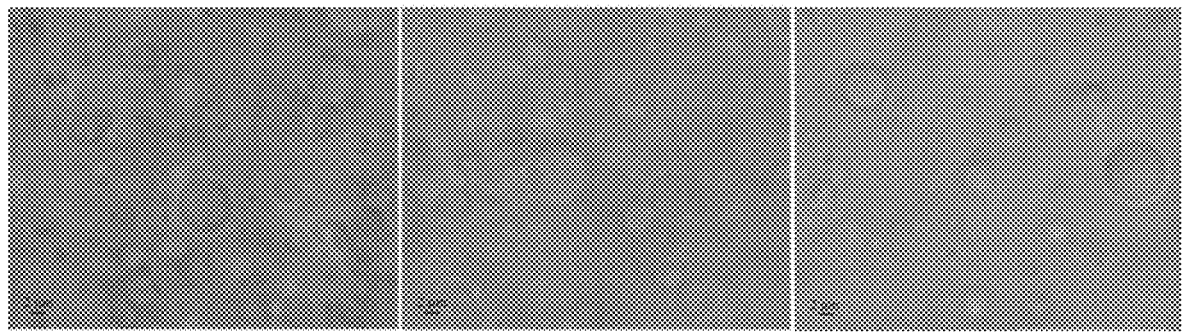
FIG. 8. Sample collected from the phase separated protein concentrate showing droplets of the concentrated silk protein (light microscopy).
Figure 9:
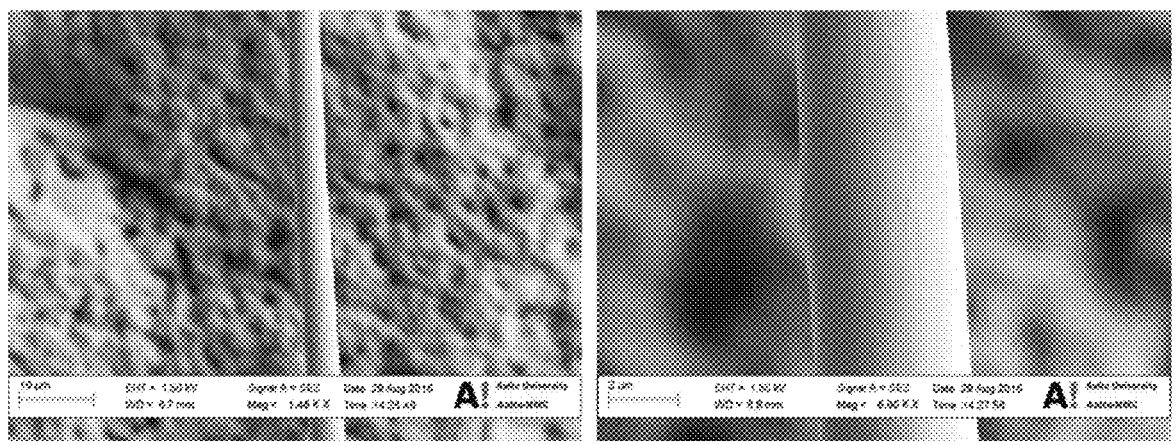
FIG. 9. Scanning electron micrograph of pulled and dried filament from the phase separated dense protein droplet.
Figure 10:
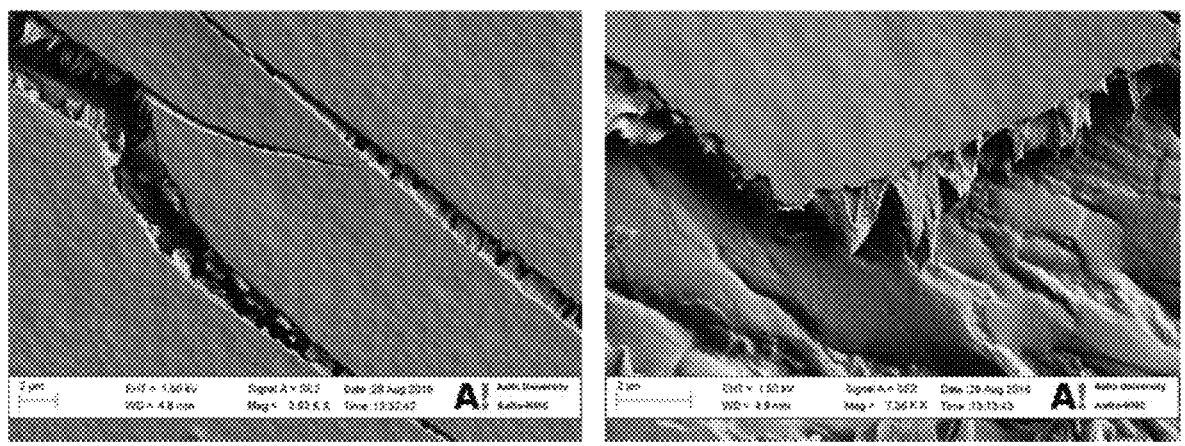
FIG. 10. Silk-like protein concentrate forms fibrous assemblies when deformed by pulling forces.
Figure 11:
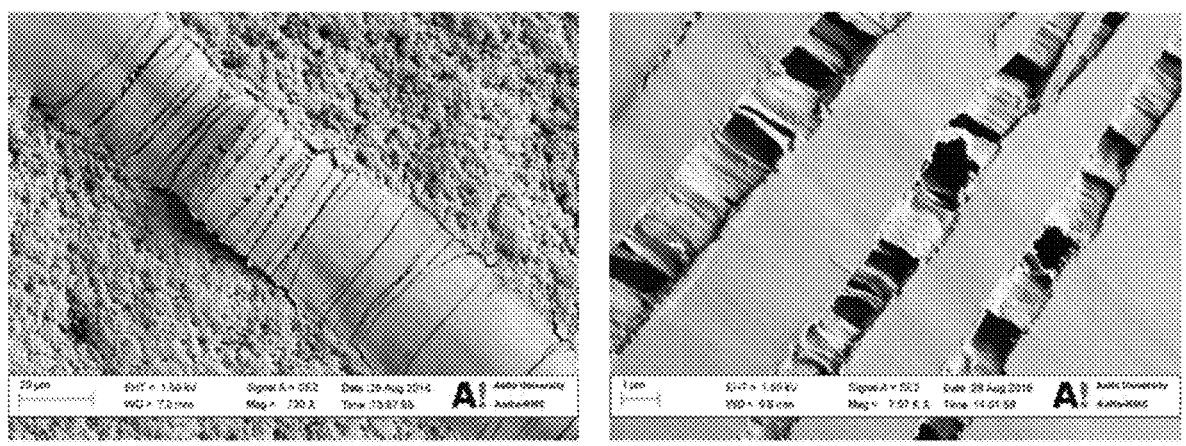
FIG. 11. Scanning electron micrograph of alignment of the molecules in the fibrous assembly formed by the silk-like molecules.

In a preferred embodiment, the method comprises a further initial step of isolating recombinant fusion protein from a host cell expressing said fusion protein. In certain embodiments the invention requires production of recombinant silk-like proteins (e.g. SEQ ID NO: 8; SEQ ID NO: 9; SEQ ID NO: 10; SEQ ID NO: 15; SEQ ID NO: 19; SEQ ID NO: 21) in a form where both the amino and carboxy ends of the silk protein have additional non-silk terminal module sequences added (FIG. 7). As discussed above, these non-silk terminal module sequences can be, for example, Cellulose-Binding-Modules (CBMs) (e.g. SEQ ID NO:7), SpyCatcher domains engineered from fibronectin-binding protein FbaB of *Streptococcus pyogenes* (e.g. SEQ ID NO:14), gamma-crystallin D from *Homo sapiens* comprising the sequence of SEQ ID NO:20 and tenth type III module of Fibronectin from *Homo sapiens* comprising the sequence of SEQ ID NO:18, variants thereof, or a mixed pair thereof (for further alternatives see Table 1). The additional protein sequences may also incorporate sequences of amino acids serving as linkers between the non-silk terminal module sequences and the silk sequence (SEQ ID NO: 5; SEQ ID NO: 6). The silk-like part can be repeats of A (SEQ ID NO: 1) and Q (SEQ ID NO: 2) sequences or naturally found sequences such as SEQ ID NO: 3 or SEQ ID NO: 4. Preferably, said spider silk protein repeat sequence comprises 10-50 silk polymer repeats, wherein the repeat sequence consists of repeat A sequence of SEQ ID NO: 1 or a variant thereof combined with repeat Q sequence of SEQ ID NO: 2 or a variant thereof. More preferably, said spider silk protein repeat sequence is (AQ)12. In another preferred embodiment, said spider silk protein repeat sequence is found in ADF3 from *Araneus diadematus* comprising the sequence of SEQ ID NO:3, the *Latrodectus hesperus* AcSp1 sequence of SEQ ID NO:4 or a variant thereof. Said linkers can preferably be selected from the group consisting of: a C-terminal linker of SEQ ID NO:6 and a N-terminal linker of SEQ ID NO:5.

In a preferred embodiment, concentration steps b) and f) of the present method are performed by a centrifugal force, dialysis such as ultrafiltration techniques, and/or evaporation. In the Examples below, centrifugal force and evaporation are used in different stages of the method.

The present invention is also providing a silk filament produced by the method of the invention. Preferably, said silk filament is composed of spider silk fusion protein as defined above. More preferably, said silk filament is composed of a spider silk fusion protein comprising 12 silk polymer repeats, wherein the repeat sequence consists of repeat A sequence of SEQ ID NO: 1 combined with repeat Q sequence of SEQ ID NO: 2, and two cellulose binding modules (CBM) from *Clostridium thermocellum* consisting of the sequence of SEQ ID NO:7 flanking said silk polymer repeats, each module linked to said repeats with a C-terminal linker of SEQ ID NO:6 or a N-terminal linker of SEQ ID NO:5. In an alternative embodiment, said silk filament is composed of spider silk protein repeat sequence ADF3 of SEQ ID NO:3, or the *Latrodectus hesperus* AcSp1 sequence of SEQ ID NO:4; and two cellulose binding modules (CBM) from *Clostridium thermocellum* consisting of the sequence of SEQ ID NO:7 flanking said silk protein repeats, each module linked to said repeat sequence ADF3 or the *Latrodectus Hesperus* AcSp1 sequence with a C-terminal linker of SEQ ID NO:6 or a N-terminal linker of SEQ ID NO:5.

The present invention is also providing a concentrate of spider silk fusion protein produced by the steps a)-f) of the method as defined above and in the claims.

The present invention is further related to a recombinant spider silk fusion protein comprising silk polymer repeats, wherein the repeat sequence consists of repeat A sequence of SEQ ID NO: 1 combined with repeat Q sequence of SEQ ID NO: 2, and two cellulose binding modules (CBM) from *Clostridium thermocellum* consisting of the sequence of SEQ ID NO:7 flanking said silk polymer repeats, each module linked to said repeats with a C-terminal linker of SEQ ID NO:6 or a N-terminal linker of SEQ ID NO:5. Preferably, the silk polymer repeat sequence is (AQ)12. More preferably, said recombinant spider silk fusion protein comprises the sequence of SEQ ID NO:8.

In an alternative embodiment, said recombinant spider silk fusion protein comprises spider silk protein repeat sequence ADF3 of SEQ ID NO:3, or the *Latrodectus Hesperus* AcSp1 sequence of SEQ ID NO:4; and two cellulose binding modules (CBM) from *Clostridium thermocellum* consisting of the sequence of SEQ ID NO:7 flanking said silk protein repeats, each module linked to said repeat sequence ADF3 or the *Latrodectus Hesperus* AcSp1 sequence with a C-terminal linker of SEQ ID NO:6 or a N-terminal linker of SEQ ID NO:5.

In a further alternative embodiment, said recombinant spider silk fusion protein comprises spider silk protein repeat sequence *Araneus diadematus* ADF3 of SEQ ID NO:3, and two SpyCatcher domains engineered from fibronectin-binding protein FbaB of *Streptococcus pyogenes* consisting of the sequence of SEQ ID NO:14 flanking said silk protein repeat sequence, each domain linked to said repeat sequence ADF3 with a C-terminal linker of SEQ ID NO:6 or a N-terminal linker of SEQ ID NO:17.

In a further alternative embodiment, said recombinant spider silk fusion protein comprises spider silk protein repeat sequence *Araneus diadematus* ADF3 of SEQ ID NO:3, and two tenth type III modules of Fibronectin from *Homo sapiens* consisting of the sequence of SEQ ID NO:18 flanking said silk protein repeat sequence, each domain linked to said repeat sequence ADF3 with a C-terminal linker of SEQ ID NO:6 or a N-terminal linker of SEQ ID NO:17.

In a further alternative embodiment, said recombinant spider silk fusion protein comprises spider silk protein repeat sequence *Araneus diadematus* ADF3 of SEQ ID NO:3, and two gamma-crystallin D domains from *Homo sapiens* consisting of the sequence of SEQ ID NO:20 flanking said silk protein repeat sequence, each domain linked to said repeat sequence ADF3 with a C-terminal linker of SEQ ID NO:6 or a N-terminal linker of SEQ ID NO:17.

A recombinant nucleic acid expressing the fusion protein as defined above and a host cell comprising said nucleic acid are in the scope of the present invention (e.g. SEQ ID NO:11; SEQ ID NO:12; SEQ ID NO:13; SEQ ID NO:16; SEQ ID NO: 22; SEQ ID NO:23).

Figure 1:
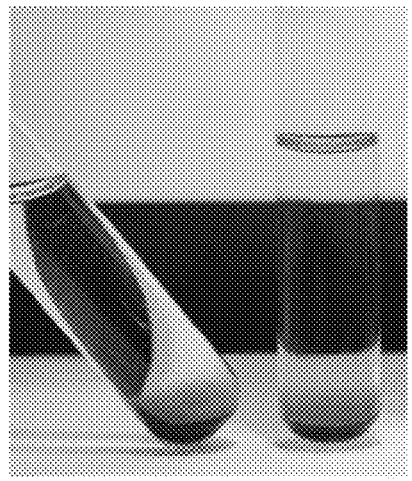
FIG. 1. Phase separation of silk-like protein into a concentrated phase. The darker liquid at the bottom is silk-like protein phase formed by concentration-induced phase separation.
Figure 2:
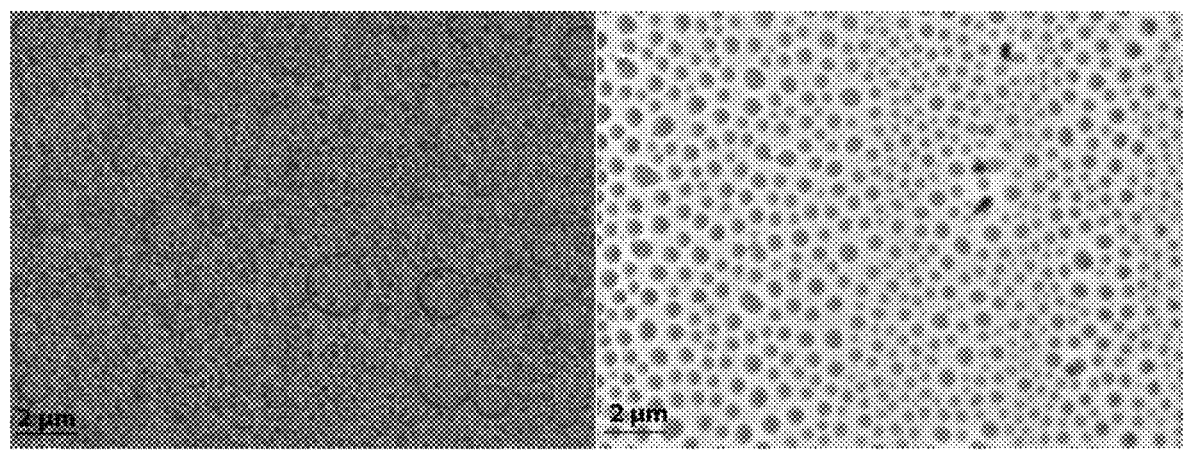
FIG. 2. Sample collected from the phase separated protein concentrate showing droplets of the concentrated silk protein (light microscopy).
Figure 3:
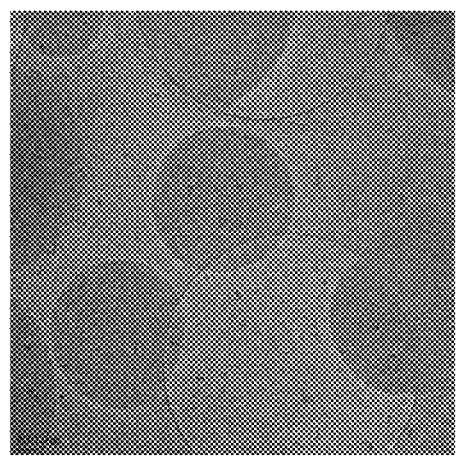
FIG. 3. Cryo-electron micrograph from the phase separated dense protein condensate droplet.

As defined above as optional step e): the solution can be clarified from cell debris and particulate matter by filtration or sedimentation by centrifugation prior to the formation of the concentrate. This step can be further enhanced by prior heating the solution to above 70 degrees Celsius. It is a distinct advantage of the invention that no precipitation of the silk-like protein is performed. The lack of a precipitation step also makes it unnecessary to involve a step of dissolving the precipitate. The use of dissolving solutions can cause damage to silk proteins and therefore the invention shows an advantage in avoiding the use of these. The omission of a precipitation of the silk-like protein and subsequent dissolving also facilitates processing and scale-up of the process. The lack of a chromatographic purification step reduces cost and makes scale-up of the process easier. The formation of the concentrate occurs as a phase separation event where the concentrate of silk-like protein distinctly forms a fluid phase that is rich in protein (see FIG. 1). This concentrate can be described as a phase separated protein solution, a dope, or also as a protein coacervate. By imaging in a microscope it is evident that sometimes the protein concentrate is visible as droplets in solution (FIGS. 2 and 3). A distinct advantage of the invention is that a high concentration of protein in the condensed phase is formed without other processing steps than a clarification and concentration step. The protein concentration in the concentrate can be further increased by for example evaporation. The protein concentrate has some distinct advantageous properties. From this concentrate it is possible to make fibers of the silk-like protein. The fibers are made by applying an extensional force on the concentrate. The extension of the concentrate leads to the formation of a fiber of silk-like protein as demonstrated in FIG. 4. The formation of fibers from the direct extension of the protein concentrate is advantageous because fibers can be formed without the need for a coagulation bath. The fibers can be formed with the surrounding medium being air, and the extrusion into a liquid is therefore not necessary. Another distinct advantageous of the protein concentrate is that it can be applied to various surfaces and it can act as water-based adhesive.

The adhesive of the present invention can be used by applying to a substrate preferably selected from the group consisting of plastics, glasses, metals, wood, paper, textiles and tissue substrates. That is, it can be used to adhere or fix the substrate. The mode of use follows the general mode of adhesive use, and the typical mode is coating.

Examples of medical or biological applications of the adhesive of the present invention are as follows, but not limited thereto: (1) orthopedic treatments such as treatment of bone, ligament, tendon, meniscus, and muscle, and implant of artificial materials; (2) treatment of perforations, lacerations, and cuts, and ophthalmic attachments such as corneal implants and artificial corneal implants; (3) dental attachments such as holding retainers, bridges, or crowns in place, securing loose teeth, repairing broken teeth, and holding fillers in place; (4) surgical treatments such as attachment of blood vessels, attachment of cellular tissue, artificial material implants, and closure of wounds; and (5) plant attachments such as bonding of transplanted parts and wound healing.

INDUSTRIAL APPLICABILITY

Silk-like proteins can be used in general to form materials such as coatings, fibers, filters, composites, automotive parts, medical materials (wound dressings, drug delivery materials, coatings, cell growth substrates). Advantages are their biocompatibility, biodegradability, the possibility to engineer and modify properties, their mechanical properties, the water-based processing, strength, toughness, and elasticity. The material can also be used for textile and clothing applications.

Adhesives have a very wide applicability in industry, for example in making composite materials, or fixing components of materials together. In a composite material, the adhesive is combined with other components and the adhesive can comprise also a minor part of the composition. In the composite material the adhesive functions as a matrix that binds the components of the material together. Other applications of an adhesive is to fix components of a device together.

Gluing applications include biomedical or medical industry. Adhesives can be used for gluing of tissue, skin, dental applications, wounds, bone, implants, sensors.

Having now generally described the invention, the same will be more readily understood by reference to the following Examples, which is provided by way of illustration and is not intended as limiting.

Although methods and materials similar or equivalent to those described herein can be used in the practice or testing of the present invention, suitable methods and materials are described below.

EXAMPLES

Example 1

Protein Production.

Plasmids (see FIG. 7) containing silk-like protein sequences (SEQ ID NO:11; SEQ ID NO:12; SEQ ID NO:13; or SEQ ID NO:16) were transformed into *E. coli* and grown in Luria Bertani (LB) media (or other bacterial growth media) until an optical density of about 0.5 AU at 600 nm is reached. Protein production was induced by adding Isopropyl β-D-1-thiogalactopyranoside (IPTG) and allowing cells to grow for 12 hours. When autoinduction media such as MAGICMEDIA™ (Thermo Fisher Scientific) was used, no isopropyl β-D-1-thiogalactopyranoside (IPTG) was added MAGICMEDIA™ is an auto induction growth media used with T7-regulated *E. coli* strains that facilitates protein expression without the addition of IPTG. Cells were broken by sonication. Alternatively, homogenizer such as Avestin Emulsiflex-C3 was used. Also, other cell lysis techniques can be used. Cell debris was removed by centrifugation.

Preparation of Solutions of Proteins.

The clarified supernatant was heated to, for example, 75 degrees Celsius to precipitate material from the supernatant, while the silk-like protein remained in solution.

As a following step, the solution containing protein was subjected to desalting using a desalting chromatography column, or alternatively using ultrafiltration. The solvent of the protein can be changed during the desalting to, for example, water or 5-50 mM Tris buffer containing 0-100 mM NaCl. The concentration of silk-like protein was determined by its optical absorbance at 280 nm.

Forming a Condensed Protein Phase.

A centrifugal concentrator at 25 degrees centigrade was used for concentrating fusion proteins solution from the previous step. During the increase in protein concentration, a phase separation occurred and a protein-rich condensed phase is formed. The protein-rich phase was collected and processed further. The phase separation occurred once the total concentration of protein solution reached around 1% w/v. The protein was then further concentrated in a second concentration step. The collected protein-rich, phase separated solution from the previous step, concentrated further gradually to approximately 10-15% w/v using a centrifugal concentrator at 25 degree Celsius and 845-1500 relative centrifugation force. To determine the concentration of proteins at these concentrations more accurate dry weight measurements were performed.

The increase in concentration can also be achieved by different types of ultrafiltration techniques, by dialysis, or by evaporation.

Third Concentration Step Using the Protein Rich-Phase.

Silk protein at a concentration of 10-15% w/v was further concentrated by evaporation in order to reach concentration of approximately 20-45% w/v.

During the concentration steps, a cleaning step may be necessary: To obtain homogenous and non-flocculating solution, aggregates, and short filaments (nanometer in diameter and couple of micrometer in length which usually form a network), and gel particles (dimensions of around couple of micrometer) were removed from the solution (by centrifugation). Removing aggregates facilitates subsequent fiber pulling or other processing.

Storage Step:

20-45% w/v is the storage concentration for the dope solution. Samples were rapidly frozen using liquid nitrogen after the third concentration step.

Example 2

Making Fibers from the Protein Concentrate.

A drop of protein solution (at approximately 30%, or 20-45%) as prepared in Example 1 was concentrated further by evaporation to 60-80% and is placed between two tip shaped objects (such as the tips of tweezers).

At around 60-80% w/v protein, a filament could be pulled from the protein solution. An example of fiber pulling is shown in FIG. 4.

Example 3

Making Adhesive from the Protein Concentrate.

Figure 13:
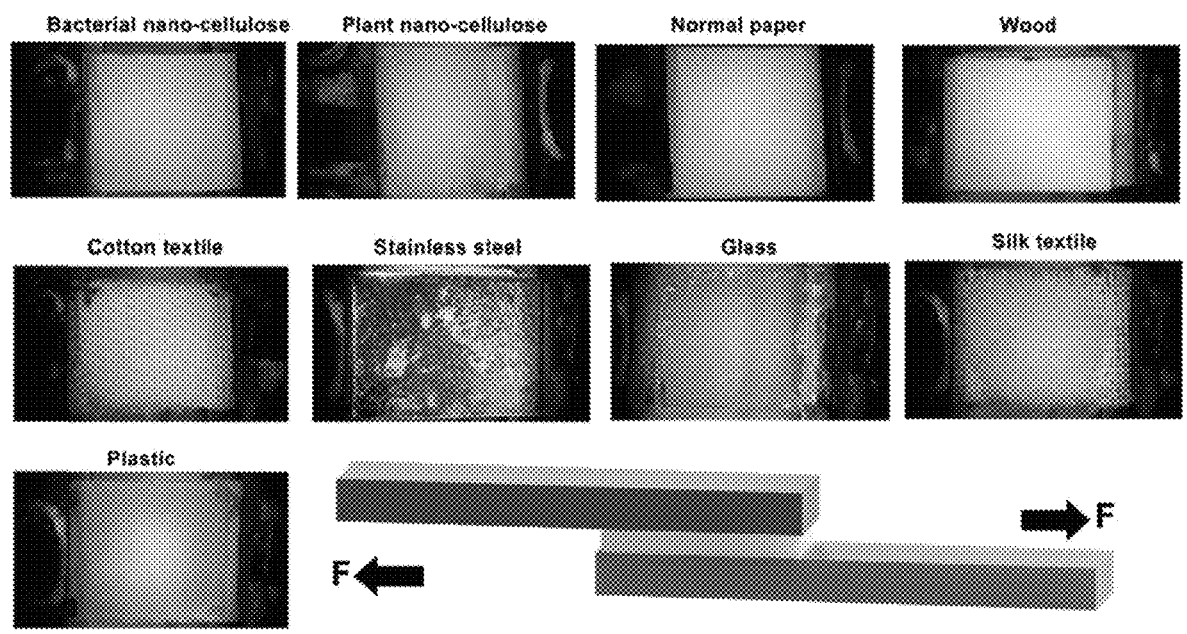
FIG. 13. Adhesion of different types of materials using the protein concentrate.
Figure 14:
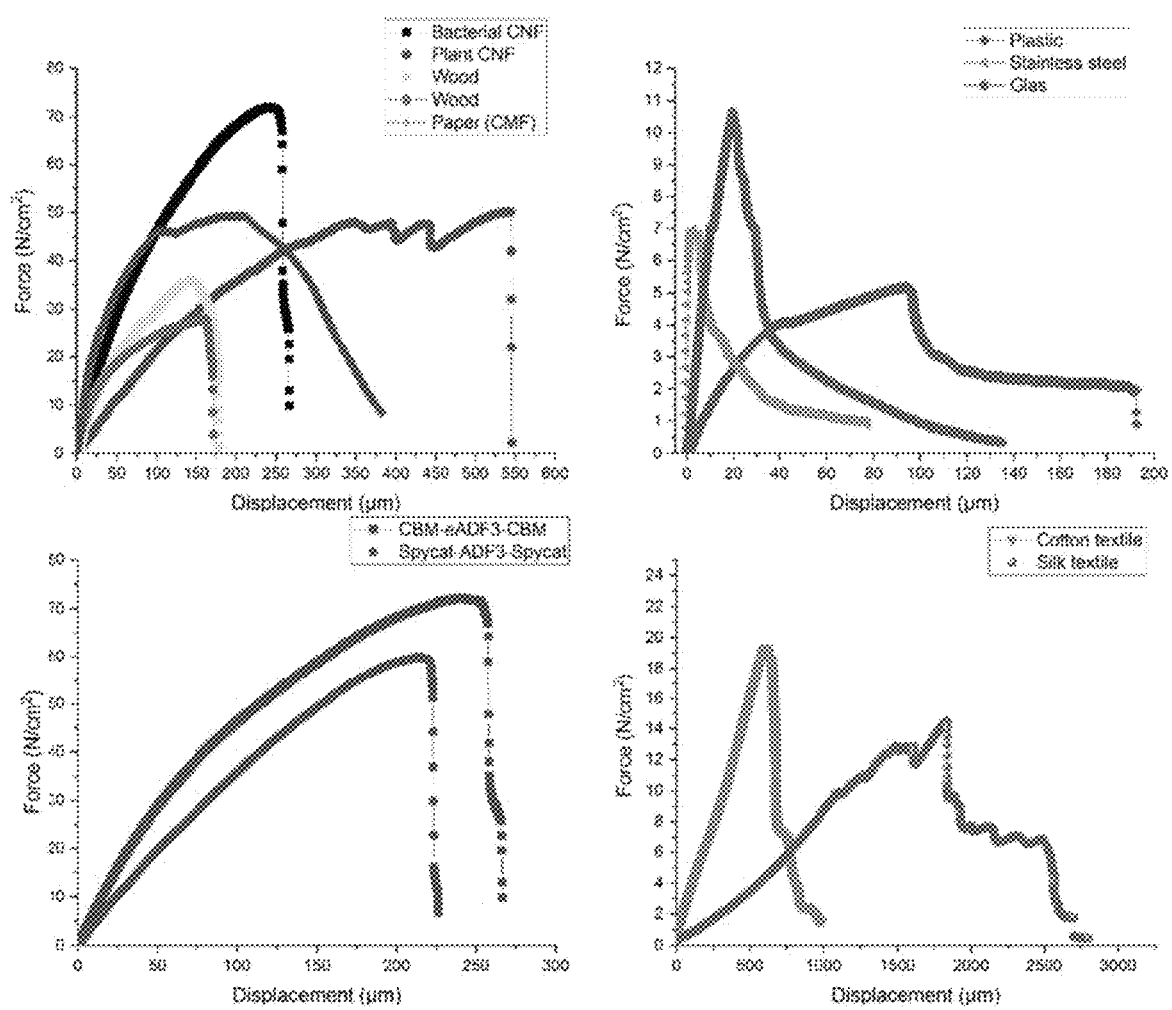
FIG. 14. The lap-shear strength of the protein concentrate adhesive for different types of materials.
Figure 15:
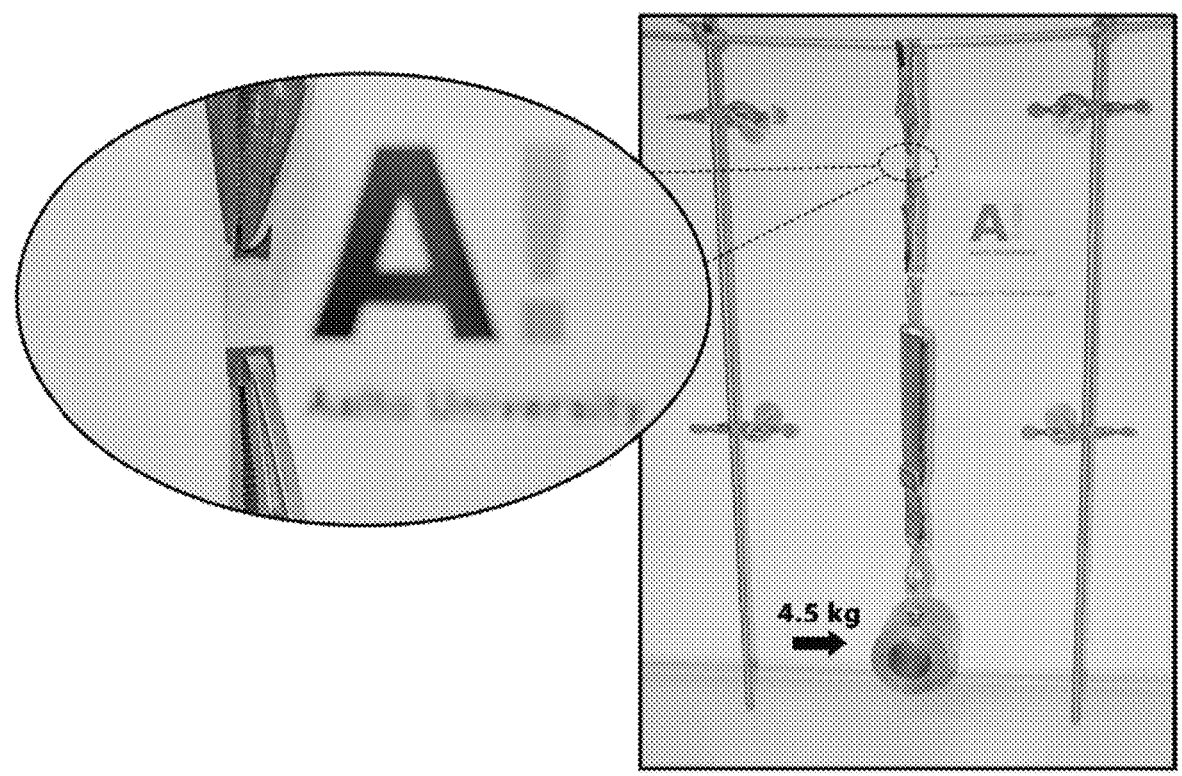
FIG. 15. Showing the strength of such joints made with protein concentrate adhesive by hanging 4.5 kg of weight from it.

A droplet of protein solution (at approximately 30% or 20-50%) as prepared in Example 1 was placed between two materials for instance normal paper and allowed to dry for 5 min until the protein concentrate solidify and glue the paper to each other. An example of protein concentrate used as an adhesive can be seen in FIG. 13.

TABLE 1

Other suitable peptides for use as non-silk terminal module sequences in a silk fusion protein of the invention.

| NO | PROTEIN | HOST | UNIPROT ID | PDB ID | SEQUENCE LENGTH (AA) | REFERENCE |
|---|---|---|---|---|---|---|
| 1 | Green fluorescence protein (GFP) | *Aequorea victoria* | P42212 | 1EMA | 239 | Ormö, M, Cubitt, A. B., Kallio, K., Gross, L. A., Tsien, R. Y., Remington, S. J. Crystal structure of the Aequorea victoria green fluorescent protein. *Science* 273, 1392-5 (1996). |
| 2 | Enhanced green fluorescence protein (EGFP) | *Aequorea victoria* | C5MKY7 | 4EUL | 239 | Arpino, J. A., Rizkallah, P. J., Jones, D. D. Crystal structure of enhanced green fluorescent protein to 1.35 a resolution reveals alternative conformations for glu222. *Plos One* 7, e47132-e47132 (2012). |
| 3 | Ubiquitin-like protein SMT3 | *Saccharomyces cerevisiae* | Q12306 | chain B in 1EUV | 98 | Mossessova, E., Lima, C. D. Ulp1-SUMO crystal structure and genetic analysis reveal conserved interactions and a regulatory element essential for cell growth in yeast. *Mol. Cell* 5, 865-76 (2000). |
| 4 | Thioredoxin 1 | *Escherichia coli* | P0AA25 | 2TRX | 109 | Katti, S. K., LeMaster, D. M., Eklund, H. Crystal structure of thioredoxin from Escherichia coli at 1.68 A resolution. *J. Mol. Biol.* 212, 167-184. (1990) |
| 5 | SnoopCatcher (residues 749-860 of adhesin RrgA's D4 domain) | *Streptococcus pneumoniae* | A0A0H2UNT6 | 2WW8 | 111 | Izore, T., Contreras-Martel, C., El-Mortaji, L., Manzano, C., Terrasse, R., Vernet, T., Di-Guilmi, A. M., Dessen, A. Structural Basis of Host Cell Recognition by the Pilus Adhesin from Streptococcus Pneumoniae. *Structure* 18, 106-15 (2010). |
| 6 | Cohesin (residues 181-340 from Cellulosomal-scaffolding protein A) | *Clostridium thermocellum* | Q06851 | 1OHZ | 162 | Carvalho, A. L., Dias, F. M. V., Prates, J. A. M., Ferreira, L. M. A., Gilbert, H. J., Davies, G. J., Romao, M. J., Fontes, C. M. G. A. Cellulosome Assembly Revealed by the Crystal Structure of the Cohesin-Dockerin Complex *Proc. Natl. Acad. Sci. USA* 100, 13809-14 (2003). |
| 7 | R2 protein (camelid antibody) | *Lama glama* | A2KD59 | 1QD0 | 128 | Spinelli, S., Frenken, L. G., Hermans, P., Verrips, T., Brown, K., Tegoni, M., Cambillau, C. Camelid heavy-chain variable domains provide efficient combining sites to haptens. *Biochemistry* 39, 1217-22 (2000). |
| 8 | Tumor necrosis factor cytokine CD40 ligand | *Homo sapiens* | P29965 | 3LKJ | 141 | Silvian, L. F., Friedman, J. E., Strauch, K., Cachero, T. G., Day, E. S., Qian, F., Cunningham, B., Fung, A., Sun, L., Su, L., Zheng, Z., Kumaravel, G., Whitty, A. Cunningham et al. Small molecule inhibition of the TNF family cytokine CD40 ligand through a subunit fracture mechanism. *ACS chemical biology* 6, 636-647. (2011): |
| 9 | Tumor necrosis factor | *Mus musculus* | Q9D777 | Chain A in 3K48 | 140 | Gordon, N. C., Lien, S., Johnson, J., Wallweber, H. J., Tran, T., Currell, B., Mathieu, M., Quan, C., Starovasnik, M. A., Hymowitz, S. G., Kelley, R. F. Multiple novel classes of APRIL-specific receptor-blocking peptides isolated by phage display. *J. Mol. Biol.* 396, 166-177. (2010). |

TABLE 1-continued

Other suitable peptides for use as non-silk terminal module sequences in a silk fusion protein of the invention.

| NO | PROTEIN | HOST | UNIPROT ID | PDB ID | SEQUENCE LENGTH (AA) | REFERENCE |
|----|---------|------|------------|--------|----------------------|-----------|
| 10 | B-cell activating factor (BAFF) | Homo sapiens | Q9Y275 | 4V46 | 148 | Kim, H. M., Yu, K. S., Lee, M. E., Shin, D. R., Kim, Y. S., Paik, S. G., Yoo, O. J., Lee, H., Lee, J.-O. Crystal structure of the BAFF-BAFF-R complex and its implications for receptor activation Nat. Struct. Biol. 10, 342-348 (2003). |

REFERENCES

1. Ebrahimi, D. et al. Silk-Its Mysteries, How It Is Made, and How It Is Used. *ACS Biomater. Sci. Eng.* 1, 864-876 (2015).
2. Nudelman, F. et al. Forming nacreous layer of the shells of the bivalves *Atrina rigida* and *Pinctada margaritifera*: An environmental- and cryo-scanning electron microscopy study. *J. Struct. Biol.* 162, 290-300 (2008).
3. Rising, A. & Johansson, J. Toward spinning artificial spider silk. *Nat. Chem. Biol.* 11, 309-315 (2015).
4. Green, M. & Sambrook, J. *Molecular cloning. A laboratory manual. Zool. Res*. (Cold Spring Harbor Laboratory Press, 2012). doi:10.3724/SP.J.1141.2012.01075
5. U.S. Pat. No. 7,951,908B2.
6. Teule, F. et al. Combining flagelliform and dragline spider silk motifs to produce tunable synthetic biopolymer fibers. *Biopolymers* 97, 418-431 (2012).
7. Adrianos, S. L. et al. *Nephila clavipes* flagelliform silk-like GGX motifs contribute to extensibility and spacer motifs contribute to strength in synthetic spider silk fibers. *Biomacromolecules* 14, 1751-1760 (2013).
8. Albertson, A. E., Teule, F., Weber, W., Yarger, J. L. & Lewis, R. V. Effects of different post-spin stretching conditions on the mechanical properties of synthetic spider silk fibers. *J. Mech. Behav. Biomed. Mater.* 29, 225-234 (2014).
9. Xia, X.-X. et al. Native-sized recombinant spider silk protein produced in metabolically engineered *Escherichia coli* results in a strong fiber. *Proc. Natl. Acad. Sci. U.S.A.* 107, 14059-63 (2010).
10. Gnesa, E. et al. Conserved C-terminal domain of spider tubuliform spidroin 1 contributes to extensibility in synthetic fibers. *Biomacromolecules* 13, 304-312 (2012).
11. Lin, S. et al. Predictive modelling-based design and experiments for synthesis and spinning of bioinspired silk fibres. *Nat. Commun.* 6, 1-12 (2015).
12. Heidebrecht, A. et al. Biomimetic Fibers Made of Recombinant Spidroins with the Same Toughness as Natural Spider Silk. *Adv. Mater.* 27, 2189-2194 (2015).
13. Téule, F. et al. A protocol for the production of recombinant spider silk-like proteins for artificial fiber spinning. *Nat. Protoc.* 4, 341-55 (2009).
14. Rammensee, S., Slotta, U., Scheibel, T. & Bausch, A. R. Assembly mechanism of recombinant spider silk proteins. *Proc. Natl. Acad. Sci. U.S.A.* 105, 6590-6595 (2008).
15. Kinahan, M. E et al. Tunable Silk: Using Microfluidics to Fabricate Silk Fibers with Controllable Properties. *Biomacromolecules* 12, 1504-1511 (2011).
16. Wong Po Foo, C. et al. Novel nanocomposites from spider silk-silica fusion (chimeric) proteins. *Proc. Natl. Acad. Sci. U.S.A.* 103, 9428-33 (2006).
17. Lang, G., Jokisch, S. & Scheibel, T. Air filter devices including nonwoven meshes of electrospun recombinant spider silk proteins. *J. Vis. Exp.* 4, e50492 (2013).
18. Hedhammar, M. et al. Structural Properties of Recombinant Nonrepetitive and Repetitive Parts of Major Ampullate Spidroin 1 from *Euprosthenops australis*: Implications for Fiber Formation †. *Biochemistry* 47, 3407-3417 (2008).
19. Tremblay, M.-L. et al. Spider wrapping silk fibre architecture arising from its modular soluble protein precursor. *Sci. Rep.* 5, 11502 (2015).
20. U.S. Pat. No. 8,173,772B2.

The invention claimed is:

1. A method for producing a condensed phase of a silk fusion protein, the method comprising the steps of:
   a) preparing a solution of a silk fusion protein in an aqueous medium, wherein said silk fusion protein is isolated from a recombinant production host and comprises a silk-like protein sequence and two separate non-silk terminal module sequences flanking said silk-like protein sequence;
   b) concentrating said silk fusion protein in said aqueous medium until a liquid phase separation occurs at about 1% w/v;
   c) collecting a protein containing phase of said aqueous medium obtained in step (b);
   d) repeating steps (b) and (c) with the protein containing phase obtained in step (c) until a protein concentration of about 20-45% w/v is reached;
   e) optionally separating aggregates of the silk fusion protein from soluble fusion proteins obtained in step (d) and removing the aggregates from the protein containing phase; and
   f) concentrating the protein containing phase obtained in step (d) or (e) to form a concentrate with a final protein concentration of about 60-80% w/v,
   wherein the steps (a) to (f) are performed so that said silk fusion protein is not precipitated and subsequently dissolved in said aqueous medium.

2. The method according to claim 1, wherein the method further comprises:
   (g) preparing silk fusion protein fibers from the concentrate obtained from step (f).

3. The method according to claim 1, wherein steps (b) and (f) are performed by centrifugal force and/or evaporation.

4. The method according to claim 1, wherein said aqueous medium is water or an aqueous buffer.

5. The method according to claim 1, wherein said silk fusion protein comprises a spider silk protein repeat sequence.

6. The method according to claim 5, wherein said spider silk protein repeat sequence comprises 10-50 spider silk polymer repeats, and wherein the repeat sequence comprises repeat A sequence of SEQ ID NO: 1 or a variant thereof combined with repeat Q sequence of SEQ ID NO: 2 or a variant thereof.

7. The method according to claim 6, wherein said spider silk protein repeat sequence is (AQ)12.

8. The method according to claim 5, wherein said spider silk protein repeat sequence is *Araneus diadematus* ADF3 comprising the sequence of SEQ ID NO:3, the *Latrodectus hesperus* AcSp1 sequence of SEQ ID NO:4 or a variant thereof.

9. The method according to claim 1, wherein said non-silk terminal module sequences flanking said silk-like protein sequence comprise cellulose binding modules (CBMs), Spy-Catcher domains, gamma-crystallin D domains, tenth type III modules of fibronectin or a mixed pair thereof.

10. The method according to claim 9, wherein said cellulose binding module (CBM) is from *Clostridium thermocellum* comprising the sequence of SEQ ID NO:7 or a variant thereof, and said SpyCatcher domain is an engineered variant of fibronectin-binding protein FbaB of *Streptococcus pyogenes* comprising the sequence of SEQ ID NO:14 or a variant thereof.

11. The method according to claim 9, wherein said cellulose binding modules or said SpyCatcher domains flanking said silk-like protein sequence are linked to said silk-like protein sequence by a linker sequence, and wherein said linker sequence is selected from the group consisting of: a C-terminal linker of SEQ ID NO:6 and a N-terminal linker of SEQ ID NO:5.

12. The method according to claim 2, wherein the fibers are prepared in step g) by pulling the fibers from the concentrate by a pulling force.

13. The method according to claim 1, wherein said non-silk terminal module sequences comprise consecutive β-strands forming a β-sheet, and wherein a length of said non-silk terminal module sequences are in a range of 90-250 amino acids.

14. The method according to claim 1, wherein said non-silk terminal module sequences comprise a pair or a mixed pair of peptides flanking said silk-like protein sequence, wherein said peptides are selected from the group consisting of: cellulose binding module (CBM), SpyCatcher domain, tenth type III module of Fibronectin, gamma-crystallin D, green fluorescence protein (GFP), enhanced green fluorescence protein (EGFP), ubiquitin-like protein SMT3, thioredoxin 1, SnoopCatcher domain, cohesin, R2 protein, tumor necrosis factor cytokine CD40 ligand, tumor necrosis factor, B-cell activating factor (BAFF) and variants or homologs thereof.

15. A method for producing a condensed phase of a silk fusion protein, the method comprising the steps of:
    a) preparing a solution of a silk fusion protein in an aqueous medium, wherein said silk fusion protein is isolated from a recombinant production host and comprises a silk-like protein sequence and two separate non-silk terminal module sequences flanking said silk-like protein sequence;
    b) concentrating said silk fusion protein in said aqueous medium until a liquid phase separation occurs at about 1% w/v;
    c) collecting a protein containing phase of said aqueous medium obtained in step (b);
    d) repeating steps (b) and (c) with the protein containing phase obtained in step (c) until a protein concentration of about 20-45% w/v is reached;
    e) optionally separating aggregates of the silk fusion protein from soluble fusion proteins obtained in step (d) and removing the aggregates from the protein containing phase; and
    f) concentrating the protein containing phase obtained in step (d) or (e) to form a concentrate with a final protein concentration of about 60-80% w/v,
wherein the steps (a) to (f) are performed so that said silk fusion protein is not precipitated and subsequently dissolved in said aqueous medium,
wherein said non-silk terminal module sequences flanking said silk-like protein sequence comprise cellulose binding modules (CBMs), SpyCatcher domains, gamma-crystallin D domains, tenth type III modules of fibronectin or a mixed pair thereof, and
wherein said cellulose binding modules or said SpyCatcher domains flanking said silk-like protein sequence are linked to said silk-like protein sequence by a linker sequence, and
wherein said linker sequence is selected from the group consisting of: a C-terminal linker of SEQ ID NO:6 and a N-terminal linker of SEQ ID NO:5.

\* \* \* \* \*